(12) United States Patent
Botti et al.

(10) Patent No.: US 8,624,044 B2
(45) Date of Patent: Jan. 7, 2014

(54) ORTHOESTER DERIVATIVES OF CROWN ETHERS AS CARRIERS FOR PHARMACEUTICAL AND DIAGNOSTIC COMPOSITIONS

(75) Inventors: Paolo Botti, Vessy/Geneva (CH); Sylvie Tchertchian, Monnetier-Mornex (FR); Doriane Theurillat, Chancy (CH)

(73) Assignee: Arisgen SA, Plan-les-Ouates (CH)

( * ) Notice: Subject to any disclaimer, the term of this patent is extended or adjusted under 35 U.S.C. 154(b) by 0 days.

(21) Appl. No.: 13/511,837

(22) PCT Filed: Nov. 25, 2010

(86) PCT No.: PCT/EP2010/068224
§ 371 (c)(1),
(2), (4) Date: Aug. 16, 2012

(87) PCT Pub. No.: WO2011/064300
PCT Pub. Date: Jun. 3, 2011

(65) Prior Publication Data
US 2012/0301401 A1    Nov. 29, 2012

(30) Foreign Application Priority Data

Nov. 25, 2009 (EP) ..................... 09014693

(51) Int. Cl.
*C07D 323/00* (2006.01)

(52) U.S. Cl.
USPC ........................................ 549/352

(58) Field of Classification Search
USPC ........................................ 549/352
See application file for complete search history.

(56) References Cited

U.S. PATENT DOCUMENTS 4,474,963 A * 10/1984 Gokel ........................ 546/178

FOREIGN PATENT DOCUMENTS

EP         1905454 A1 *  9/2006 ............ A61K 47/22
EP         1 905 454 A1     4/2008

OTHER PUBLICATIONS

Hasse et al. Sensors and Activators B, 18-19, 383-386, 1994.*
Hasse, W., et al., PbOH+-Selective Membrane Electrode Based on Crown Ethers, Sensors and Actuators B, 1994, 18-19:383-386.
International Application No. PCT/EP2010/068224, International Search Report and Written Opinion of the International Searching Authority dated Jan. 25, 2011.

* cited by examiner

Primary Examiner — Nizal Chandrakumar
(74) Attorney, Agent, or Firm — Pillsbury Winthrop Shaw Pittman LLP

(57) ABSTRACT

This invention relates to A crown ether of formula (I)

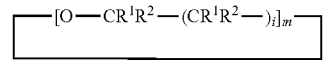

wherein m is 4, 5, 6, 7, or 8 and i is, independently for each occurrence, 1 or 2; each occurrence of $R^1$ and $R^2$ is independently selected from hydrogen; linear or branched and substituted or unsubstituted $C_1$ to $C_{10}$ alkyl, alkenyl and alkinyl; and substituted or unsubstituted aryl with up to 10 ring atoms; or $R^1$ and $R^2$ together form an oxo group; at least one occurrence in the crown ether of $R^1$, $R^2$ and the carbon to which $R^1$ and $R^2$ are attached, said carbon being bound directly to an ether oxygen of formula (I), form together a group of formula (II)

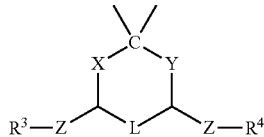

wherein L is a linker which is absent or selected from a covalent bond and $(CR^5R^6)_n$, each occurrence of $R^5$ and $R^6$ being independently selected from hydrogen; linear or branched and substituted or unsubstituted $C_1$ to $C_{10}$ alkyl, alkenyl and alkinyl; and substituted or unsubstituted aryl with up to 10 ring atoms, n being 1, 2 or 3; X and Y, independently from each other, are selected from O and S; Z, independently for each occurrence, is absent or an electron-withdrawing group; $R^3$ and $R^4$, independently for each occurrence, are selected from hydrogen; linear or branched and substituted or unsubstituted $C_1$ to $C_{10}$ alkyl, alkenyl and alkinyl; substituted or unsubstituted aryl with up to 10 ring atoms; $H(OCH_2CH_2)_k$— and $H(OCH_2CH_2)_kO$—, wherein k is an integer number from 1 to 10; wherein substituents, if present, are selected from OH, O—$CH_3$ and halogens.

3 Claims, No Drawings

ORTHOESTER DERIVATIVES OF CROWN ETHERS AS CARRIERS FOR PHARMACEUTICAL AND DIAGNOSTIC COMPOSITIONS

RELATED APPLICATIONS

This application is the National Phase of International Application No. PCT/EP2010/068224, filed Nov. 25, 2010, which designated the U.S. and that International Application was published under PCT Article 21(2) in English, and claims priority to European Application No. 09014693.7, filed Nov. 25, 2009, all of which applications are incorporated herein by reference in their entirety.

This invention relates to a crown ether of formula (I)

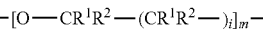

wherein m is 4, 5, 6, 7, or 8 and i is, independently for each occurrence, 1 or 2; each occurrence of $R^1$ and $R^2$ is independently selected from hydrogen; linear or branched and substituted or unsubstituted $C_1$ to $C_{10}$ alkyl, alkenyl and alkinyl; and substituted or unsubstituted aryl with up to 10 ring atoms; or $R^1$ and $R^2$ together form an oxo group; at least one occurrence in the crown ether of $R^1$, $R^2$ and the carbon to which $R^1$ and $R^2$ are attached, said carbon being bound directly to an ether oxygen of formula (I), form together a group of formula (II)

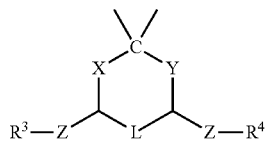

wherein L is a linker which is absent or selected from a covalent bond and $(CR^5R^6)_n$, each occurrence of $R^5$ and $R^6$ being independently selected from hydrogen; linear or branched and substituted or unsubstituted $C_1$ to $C_{10}$ alkyl, alkenyl and alkinyl; and substituted or unsubstituted aryl with up to 10 ring atoms, n being 1, 2 or 3; X and Y, independently from each other, are selected from O and S; Z, independently for each occurrence, is absent or an electron-withdrawing group; $R^3$ and $R^4$, independently for each occurrence, are selected from hydrogen; linear or branched and substituted or unsubstituted $C_1$ to $C_{10}$ alkyl, alkenyl and alkinyl; substituted or unsubstituted aryl with up to 10 ring atoms; $H(OCH_2CH_2)_k$— and $H(OCH_2CH_2)_kO$—, wherein k is an integer number from 1 to 10; wherein substituents, if present, are selected from OH, O—$CH_3$ and halogens.

In this specification, a number of documents including patent applications and manufacturer's manuals is cited. The disclosure of these documents, while not considered relevant for the patentability of this invention, is herewith incorporated by reference in its entirety.

An increasing number of drugs is of peptidic or proteinaceous nature. These drugs in many cases have a limited shelf life and/or their administration can only be effected in an invasive manner. Intravenous administration in turn often entails significant degradation of the drug in the liver. The latter could be avoided if it were possible to deliver the drug in a manner which circumvents the degradation system of the liver. Furthermore, non-invasive administration is less cumbersome and more convenient for patients and medical staff. However, non-invasive administration, for example by the oral, buccal, sublingual, nasal, pulmonary, dermal or transdermal route is precluded for many drugs, in particular peptides and proteins, because they carry electrostatic charges. The presence of electrostatic charges renders cell membranes an insurmountable barrier for these drugs. Covalent modification to remove the charges may have deleterious effects, including misfolding of the polypeptide structure. An other disadvantage of covalent modification is that a compound is obtained by said modification which is distinct from the drug for which approval has been obtained.

Cyclic polyesters (polylactones) are known in the literature as cation ionophores. For example, nonactine and tetranactine are macrotetrolide antibiotics that coordinate metal ions. Other types of cyclic polyesters (polyglycolic or lactic esters) have been studied by ab initio molecular orbital calculation and have been found, depending on the number of units (size of the ring) to accommodate certain cations with some selectivity (McGeary and Bruget (2000), Lifson et al. (1983), Lifson et al. (1984)).

Cyclic polyethers or crown ethers are known in the literature to complex cations. For example, 18-crown-6 is a cyclic polyether known to complex many cations including $Na^+$, $K^+$ and $NH_4^+$.

There is an unmet need for modifying drugs, in particular peptidic or proteinaceous drugs, drugs which are nucleic acids such as siRNAs as well as drugs comprising cations, to enhance their formulation and, related thereto, their administration properties. The term "administration properties" is understood to include the available routes of administration for a given active agent in a given formulation.

The technical problem underlying the present invention was the provision of means and methods for modifying the formulation properties of pharmaceutically or diagnostically active agents.

Accordingly, this invention relates to a crown ether of formula (I)

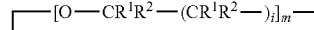

wherein m is 4, 5, 6, 7, or 8 and i is, independently for each occurrence, 1 or 2;

each occurrence of $R^1$ and $R^2$ is independently selected from hydrogen; linear or branched and substituted or unsubstituted $C_1$ to $C_{10}$ alkyl, alkenyl and alkinyl; and substituted or unsubstituted aryl with up to 10 ring atoms; or $R^1$ and $R^2$ together form an oxo group;

at least one occurrence in the crown ether of $R^1$, $R^2$ and the carbon to which $R^1$ and $R^2$ are attached, said carbon being bound directly to an ether oxygen of formula (I), form together a group of formula (II)

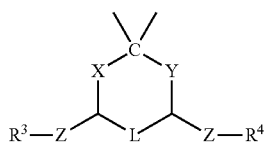

wherein

L is a linker which is absent or selected from a covalent bond and $(CR^5R^6)_n$, each occurrence of $R^5$ and $R^6$ being independently selected from hydrogen; linear or branched and substituted or unsubstituted $C_1$ to $C_{10}$ alkyl, alkenyl and alkinyl; and substituted or unsubstituted aryl with up to 10 ring atoms, n being 1, 2 or 3;

X and Y, independently from each other, are selected from O and S;

Z, independently for each occurrence, is absent or an electron-withdrawing group;

$R^3$ and $R^4$, independently for each occurrence, are selected from hydrogen; linear or branched and substituted or unsubstituted $C_1$ to $C_{10}$ alkyl, alkenyl and alkinyl; substituted or unsubstituted aryl with up to 10 ring atoms; $H(OCH_2CH_2)_k$— and $H(OCH_2CH_2)_kO$—, wherein k is an integer number from 1 to 10;

wherein substituents, if present, are selected from OH, O—$CH_3$ and halogens. Preferred halogens are F, Cl and Br.

The rectangular line in formula (I) stands for one covalent single bond connecting the oxygen atom of the first occurrence of the moiety in square brackets with the last carbon atom of the last occurrence of the moiety in square brackets.

The building block in square brackets is repeated m times. A preferred value of m is 6. Further preferred values are 5 and 7. Each building block, depending on the value of i, comprises two or three carbon atoms forming the crown ether ring, wherein preference is given to i=1, i.e., two carbon atoms of each building block contributing to the crown ether ring. The terms "crown ether ring", "crown ether macrocycle" and "ring structure of said crown ether" refer to the ring or macrocycle formed by all oxygens and carbons shown in formula (I). In case of the preferred embodiment of m being 6 and i being 1, this ring or macrocycle is the ring or macrocycle of 18-crown-6, i.e., it comprises 6 oxygens and 12 carbons, giving rise to an 18-membered macrocycle.

In addition to the orthoester functionality, the crown ether may be further modified by $R^1$ and $R^2$ as defined above. Within the definition of $R^1$ and $R^2$, linear alkyl, alkenyl and alkinyl groups are preferred over branched alkyl, alkenyl and alkinyl groups. Furthermore, unsubstituted groups $R^1$ and $R^2$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl.

Preference is given to embodiments wherein each occurrence of $R^1$ and $R^2$, to the extent they do not form a group of formula (II), is hydrogen. In further preferred embodiment, each of $R^1$ and $R^2$, to the extent they do not form a group of formula (II) and not an oxo group, is hydrogen.

In the crown ethers of formula (I), at least one carbon atom which is bound directly to an ether oxygen of formula (I) is modified as required by formula (II). As a consequence, the crown ether comprises at least one orthoester or a thio-analogue thereof. In thio-analogues, one or both of X and Y are S. As used in the following, the term "orthoester" embraces said thio-analogues. The orthoester can be seen as a derivative of one equivalent of a crown ether having a carbonyl group adjacent to an ether oxygen—such crown ether comprising an ester group—and two equivalents of an alcohol or thiol. It is understood that the carbon atom with two free valences as shown in formula (II) is part of the crown ether ring.

If the linker L is present, the orthoester is cyclic. The cycle comprises X and Y. Cyclic orthoesters can be considered as derivatives of a crown ether comprising an ester group, said derivative being obtainable by treating said crown ether comprising an ester group with a diol (or glycol) or a thioanalogue thereof such as a dithiol. Also alcohols with one hydroxy and one thiol group are envisaged and subsumed under the term "thioanalogue of a diol". In case of a vicinal diol or thioanalogue thereof such as ethylene glycol or propylene glycol, L in the resulting cyclic orthoester is a covalent bond. In case of an N,N+2 diol (N and N+2 being the numbers of the carbon atoms carrying the hydroxy groups) or thio-analogue thereof, N+2 not exceeding the number of carbon atoms in said diol or thio-analogue thereof, L in the resulting cyclic orthoester is a methylene group or $CR^5R^6$, $R^5$ and $R^6$ being defined above and further specified below. Similarly, in case of an N,N+3 diol or thio-analogue thereof, N+3 not exceeding the number of carbon atoms in said diol or thio-analogue thereof, L in the resulting cyclic orthoester is $CH_2CH_2$ or $CR^5R^6CR^5R^6$, $R^5$ and $R^6$ being defined above. Said thiol or thio-analogue thereof may comprise further functional groups. Within the definition of $R^5$ and $R^6$, linear alkyl, alkenyl and alkinyl groups are preferred over branched alkyl, alkenyl and alkinyl groups. Furthermore, unsubstituted groups $R^5$ and $R^6$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl. As indicated above, preference is furthermore given to embodiments wherein each occurrence of $R^5$ and $R^6$ is hydrogen.

A preferred vicinal diol comprising further functional groups is tartaric acid; see, for example, formulae (III) to (VI), (VIII) and (IX). As shown in particularly preferred structures below, the carboxylic groups of the tartaric acid moiety of an orthoester may be esterified with an alcohol, e.g. glycerol or ethanol; see, for example formulae (VIII) and (IX). In that case the electron-withdrawing groups Z are ester groups. The free hydroxyl groups of glycerol are available for further derivatization, if desired. Such further derivatization may include the attachment of polymers or oligomers such as polyethylene glycol (PEG) or esterification with fatty acids, said fatty acids preferably being saturated or unsaturated $C_4$ to $C_{20}$ alkanoic acids. Such further derivatisation may be useful in enhancing or modifying biocompatibility and/or delivery across membranes, mucosae, or to target sites within a cell or an organism.

A further preferred vicinal diol comprising further functional groups is 2,3-dihydroxy-propanoic acid; see, for example, formula (XI). The carboxylic group of 2,3-dihydroxy-propanoic acid may be further derivatized, for example esterified; see, for example, the option for R in formula (XI).

If L is absent, X and Y do not form part of a cycle. In that case, the free valences of the carbon atoms bound to X or Y, respectively and bearing Z (or $R^3$ and/or $R^4$ in case of absence of Z) are saturated with hydrogens. If L is absent, the orthoesters can be considered as derivatives of a crown ether comprising an ester group and an alcohol or thiol or mixtures thereof. Preferred crown ethers of the invention comprising acyclic orthoesters are the crown ethers of formulae (VII) and (X). An example of the compound of formula (X) is shown in formula (XII) below.

Z is an electron-withdrawing group which may be absent in one or both occurrences. If Z is absent, $R^3$ and/or $R^4$ are directly bound to the carbon atom which in turn is directly bound to X or Y, respectively. Preference is given to one or two occurrences of Z being present within one group of formula (II).

Within the definition of $R^3$ and $R^4$ linear alkyl, alkenyl and alkinyl groups are preferred over branched alkyl, alkenyl and alkinyl groups. Furthermore, unsubstituted groups $R^3$ and $R^4$ are preferred. The term "substituted" refers to the presence of substituents, said substituents being selected from OH and halogen. Within alkyl, alkenyl and alkinyl, preference is given to alkyl. Preferred chain length of alkyl, alkenyl and alkinyl are $C_1$ to $C_6$, more preferred $C_1$ to $C_4$. Aryl preferably is a five- or six-membered ring. Preferred aryl groups include phenyl. As regards $H(OCH_2CH_2)_k$— and $H(OCH_2CH_2)_kO$—, preference is given to the following values of k: 1, 2, 3, 4 and 5. Particularly preferred values of k are 3 and 5.

In preferred embodiments, $R^3$ and $R^4$, independently for each occurrence, are selected from hydrogen, methyl, ethyl, n-propyl, i-propyl and $(H(OCH_2CH_2)_5$—). Particularly preferred is that $R^3$ and/or $R^4$ is ethyl.

If Z is present, $H(OCH_2CH_2)_k$— is the preferred option of $H(OCH_2CH_2)_k$— and $H(OCH_2CH_2)_kO$—. It is understood that the crown ethers of the invention do not comprise peroxide groups. If Z is absent, $H(OCH_2CH_2)_kO$— is the preferred option of $H(OCH_2CH_2)_k$— and $H(OCH_2CH_2)_kO$—.

The crown ethers of formula (I) exhibit ether functional groups and at least one orthoester functional group. Lone electron pairs of the oxygens are available for forming a complex with a ligand. The envisaged ligands are detailed further below. Of particular relevance for complexation are ether oxygens which do not have an electron-withdrawing group (such as a carbonyl group) in their immediate vicinity. In this respect, the cyclic compounds of the invention resemble crown ethers of the prior art (see above). Crown ethers of the prior art, in particular those in which ether groups are the only oxygen-containing functional groups, while suitable for complexation, however, have the disadvantage that they are not biodegradable or not biodegradable to a sufficient extent.

Regarding the orthoester functional group(s), we note that orthoesters are amenable to hydrolysis in organisms and accordingly biodegradable. Elimination (also referred to as "clearance") of the orthoester is further facilitated in presence of one or two electron-withdrawing groups (designated "Z"). Particularly preferred Z groups are esters, which upon hydrolysis yield groups which are negatively charged at physiological pH, thus permitting more rapid elimination of the orthoester. To explain further, two ester groups (with the carbonyl group of the ester group being directly bound to the cyclic structure indicated in formula (II)) generate two negatively charged carboxylates, thereby further facilitating elimination. Degradation of the crown ether according to the invention may yet be further facilitated by the presence of one or more oxo groups as defined above.

As such, the crown ethers according to the invention provide an advantageous compromise between complexation capability and biodegradability as conferred by one or more orthoester functional groups.

Accordingly, the compounds according to the invention are biodegradable and biocompatible. The term "biodegradable" refers to substances which are degradable in living organisms. The term "biocompatible" denotes substances which do not give rise to adverse reactions of the human or animal body, preferably neither in their intact form nor when degraded. The term "biocompatible" is equivalent to "generally recognized as safe (GRAS)". Means for assessing biocompatibility are well known in the art, include in vitro tests performed on cell lines, in vivo tests on animals as well as clinical tests on human beings and do not have to be further detailed here. Any test required or recommended by regulatory authorities for the assessment of whether a compound is generally recognized as safe (GRAS), is preferably employed.

Biodegradability may be expressed in quantitative terms for example in terms of the half-life of a crown ether of the invention in plasma. Means and methods for determining half-life in plasma are known in the art. For example, a crown ether is mixed with plasma from a plasma pool and subsequently incubated at 37° C. while agitating. At given time-points, aliquots are removed and analyzed by HPLC.

The term "half-life" refers to period of time required for the opening of the ring structure of formula (I). Typically, the following series of reactions occurs in plasma or under physiological conditions. First, hydrolysable groups Z such as ester groups are hydrolyzed if present. If the carbonyl group of the ester group is directly bound to the cyclic structure of formula (II), hydrolysis generates a carboxylate attached to the orthoester. Subsequently, and facilitated by the carboxylate, the orthoester is eliminated. As a consequence, the ring structure of formula (I) opens. If Z is absent in all occurrences, the orthoester elimination will generally be the first reaction to occur (in that case without facilitation by a electron-withdrawing group). In either case, the opening of the ring is the event which is determined when determining half-life in plasma or under physiological conditions. Accordingly, biodegradability refers to the capability of the ring to open in a biological environment, more specifically in plasma or under physiological conditions. Examples of physiological conditions are given below.

Upon opening of the ring, further reactions, leading to further degradation will follow. If more than one orthoester is present, and all orthoesters have the same structure, it is expected that elimination of the remaining orthoesters will rapidly follow the elimination of the first orthoester. In case the orthoesters are different in structure, the elimination of the more stable orthoesters, for example those with only one or no group Z present, will occur in a delayed manner on average. If only one orthoester is present, further degradation may be facilitated by the presence of one or more oxo groups as defined above. According to a preferred embodiment, the carbon atom bearing the oxo group is directly adjacent to an ether oxygen of the ring structure of the crown ether, thereby giving rise to an ether group. Such an ester group is hydrolysable in plasma and under physiological conditions.

In a preferred embodiment, the half-life of a crown ether of the invention in plasma is shorter than 24 hours, more preferably shorter than 12 hours, 6 hours, 3 hours, 2 hours, 1 hour, 30 min, 20 min, 10 min or 5 min. The term "biodegradable" refers to degradation of said crown ether, wherein it is understood that degradation consists of or includes cleavage or hydrolysis of a least one orthoester group of said crown ether.

The terms "complex" and "complexation" are well known in the art and refer to a reversible association of molecules, atoms, or ions through non-covalent chemical bonds. Usually two interaction partners, a complexing agent having a plurality of functional groups and a small molecule, atom or ion bound by said plurality of functional groups are implied. As used herein, the term complex is not confined to metal ions bound to a complexing agent. It relates in general to complexes between a compound of the invention and a cation or cationic group also referred to as ligand. The crown ethers of the invention provide oxygen-containing functional groups, the oxygen being available for complex formation.

In the following, crown ethers according to the invention are sometimes referred to as "compounds" of the invention or "cyclic compounds" of the invention. Furthermore, it is understood that preference is given to crown ether which are capable of improving at least one of the following: (a) transmembrane and/or transmucosal delivery; (b) solubility in non-aqueous solvents; and (c) stability of an agent, said agent being further defined below. Also, it is understood that any description or graphical representation of compounds of the invention refers to such compounds to the extent valence and stability permit.

The term "transmembrane delivery" relates to the capability of said active agent to cross cell membranes. Since cell membranes comprise a hydrophobic layer formed by the lipophilic parts of membrane lipids, charged molecules do not readily cross the membrane. As a consequence, delivery across membranes is negligible or zero. It is understood that an improvement of the transmembrane delivery also entails an improvement of, for example, transdermal delivery and transepithelial delivery.

The term "transmucosal delivery" relates to the capability of said active agent to cross the mucosa. Any mucosa is envisaged, including the mucosa of mouth, stomach, intestine, nose and lungs. Since any mucosa comprises cell membranes, the considerations relating to cell membranes above apply to mucosa as well.

The term "improved solubility" refers to any increase of solubility in said non-aqueous solvent. Preferably, the increase in solubility is 1,2-fold; 1,5-fold, twofold, threefold, fourfold, fivefold, tenfold, hundredfold or thousandfold. Also increases in solubility by more than three orders of magnitude are deliberately envisaged.

The term "non-aqueous solvent" as used herein relates to solvents which are not on an aqueous basis. The term "non-aqueous solvent" includes anhydrous solvents, but is not confined thereto. In other words, the non-aqueous solvent may comprise traces of water. Preferably, the amount of water is less than 5 vol.-%, then 2% vol.-%, 1% vol.-%, more preferred less than 0.5 vol.-%, less than 0.1 vol.-%, less than 0.01 vol.-% or less than 0.001 vol.-%. The term includes organic solvents, in particular apolar organic solvents, organic solvents with a smaller dipole moment than water as well as organic solvents which are hydrophobic, i.e. solvents which are hardly or not at all miscible with water. The term "organic solvent" is known in the art and relates to carbon-based substances commonly used in the chemical industry, capable of dissolving or dispersing one or more substances. Generally speaking, organic solvents are more lipophilic or hydrophobic than water. As a consequence, their logP values are generally greater than zero. Organic solvents according to the invention refer to unsubstituted hydrocarbon solvents like paraffinic, aliphatic and aromatic hydrocarbons and their derivatives containing heteratoms, like oxygen (e.g. alcohols, ketones, glycol esters), halogens (e.g. carbon tetrachloride), nitrogen (e.g. DMF, dimethyl formamide and acetonitrile) or sulphur (e.g. DMSO: dimethyl sulfoxide). Commonly used organic solvents are methanol, ethanol, propyleneglycole (PG), glycerol, alcohols from $C_3$ to $C_{10}$, acetonitrile, butanone, 1,1,1-trifluoroethanol (TFE), hexafluoroisopropanol (HFIP), ethyl acetate, carbon tetrachloride, butanol, dibutyl ether, diethyl ether, cyclohexane, methylene chloride (dichloromethane), hexane, butyl acetate, di-isopropyl ether, benzene, dipentyl ether, chloroform, heptane, tetrachloroethylene, toluene, hexadecane, dimethylformamide (DMF), N-methylpyrrolidone (NMP), dimethylacetamide (DMA), tetrahydrofurane (THF) and dioxane.

Preferred non-aqueous solvents according to the invention include solvents which may be used as a constituent in a pharmaceutical or diagnostic composition and/or solvents which may be used during the course of the manufacture and formulation of said pharmaceutical or diagnostic composition. In other words, the medical use of such solvents is approved and/or their use does not pose a threaten to the health of an individual to be treated. Specific non-aqueous solvents which are deliberately envisaged include organic solvents described above. The term "non-aqueous solvent" also includes natural products such as oils including olive oil and fatty acids, which may be saturated or non-saturated. Another preferred non-aqueous solvent is a FDA approved hydrophobic vehicle or diluent, such as for example, but not limited to Cremofor EL and acyl glycerols, in particular C6- to C24-acyl glycerols or C6- to C20-acyl glycerols. According to the invention, acyl gylcerols may be saturated and unsaturated. Of particular interest are C8- to C10-mono-acyl glycerols and C21-C24 unsaturated mono acyl glycerols.

The term "stability" includes the shelf life of the active agent in pure form or of formulations comprising the active agent. As such, the term "stability" relates to stability in both solid form (pure complex or solid pharmaceutical or diagnostic composition) of the active agent as well in liquid/solution form (including liquid formulations). It furthermore includes thermostability as well as stability against enzymatic degradation. The term "stability" includes maintenance of biological, pharmaceutical and/or diagnostic activity. The term "stability" also refers to stability of the constituents or functional food or food supplements described herein below. It has to be understood that improvement of stability of said active agent is not an obvious consequence of or extrapolation from an improvement of transmembrane or transmucosal delivery. In fact, for the improvement of stability the modulation by the cyclic compound of the interaction between molecules of the active agent is relevant as opposed to the modulation of the interaction between the active agent and the environment in a membrane or mucosa. This is particularly advantageous for easily degradable active molecules, including nucleic acids such as RNAi agents.

The crown ethers according to the invention have the further advantage that their interaction (complex formation) with an active agent (further detailed below) is transient. The term "transient" as used herein refers to reversibility under physiological conditions. Upon passage of the cell membrane, mucosa and/or skin, the cyclic compounds either detach from the active agent, for example as a consequence of the presence of competing ligands such as ammonium ions or primary or secondary amides, and/or they are degraded.

In a preferred embodiment, at least one occurrence in the crown ether of $R^1$ and $R^2$ together form an oxo group.

It is understood that (i) no acid anhydride is present in those cases where more than one oxo group is present, and (ii) an oxo group and a group of formula (II) are not present at the two positions adjacent to the same ether oxygen, noting that in such a case an anhydride would be formed upon hydrolysis of the orthoester comprising the group of formula (II).

In a further preferred embodiment, the ring structure of said crown ether is provided by 18-crown-6, 12-crown-4, 13-crown-4, 14-crown-4, 15-crown-5, 16-crown-5, 17-crown-5, 20-crown-6, 21-crown-7 or 24-crown-8. Particularly preferred is 18-crown-6.

In a further preferred embodiment, one or two oxo groups are present.

It is preferred that the carbon atom bearing the oxo group is directly adjacent to an ether oxygen atom of the ring structure of said crown ether, thereby given rise to an ester group.

In a further preferred embodiment, the number of ether oxygen atoms in the ring is an even number and one oxo group is present adjacent to every other ether oxygen atom.

In a further preferred embodiment, (a) one group of formula (II) and two oxo groups; (b) two groups of formula (II) and one oxo group; or (c) three groups of formula (II) and no oxo group are present. In a particularly preferred embodiment, the ring structure of said crown ether is provided by 18-crown-6 and the three groups according to any of options (a) to (c) are located on every other building block, said building block being the group in square brackets of formula (I) above. More preferably, the three groups according to any of options (a) to (c) are located such that a three-fold symmetry is present. An example of three-fold symmetry is shown below.

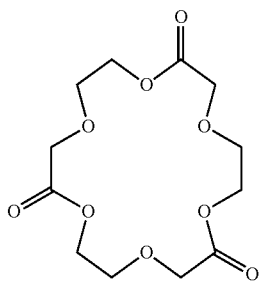 [SMILES: O=C1COCCOC(=O)COCCOC(=O)COCCO1]

According to the embodiment described above, one, two or three of the displayed oxo groups are replaced with a group of formula (II).

In an alternative preferred embodiment, (a) one group of formula (II) and one oxo group are present, wherein the carbon atom of said group of formula (II), said carbon atom being part of the ring structure of the crown ether, is directly bound to the carbon atom bearing the oxo group; or (b) two groups of formula (II) are present, wherein the two carbon atoms of said two groups of formula (II), said carbon atoms being part of the ring structure of the crown ether, are directly bound to each other.

This embodiment includes embodiments, wherein the crown ether can be seen to comprise an oxalic acid moiety, wherein both carboxyl groups of said oxalic acid moiety are involved in ester bonds within the crown ether ring, and furthermore one or two of said ester bonds is modified to be an orthoester. Particularly preferred crown ethers of this type are the crown ethers of formulae (V) to (VII).

In a further preferred embodiment, L is a covalent bond.

In a further preferred embodiment, both X and Y are O.

In a preferred embodiment, Z is selected from —O—C(=O)—, —C(=O)—O— and —C(=O)—. Particularly preferred is that $R^3$Z and/or $R^4$Z are $R^3$—O—C(=O)— and/or $R^4$—O—C(=O)—.

In a further preferred embodiment, $R^3$ and $R^4$ are independently selected from hydrogen, methyl, ethyl, n-propyl, i-propyl, 2,3-dihydroxy-propyl, and H(OCH$_2$CH$_2$)$_5$—. In a more preferred embodiment, $R^3$ and $R^4$ are selected to be the same.

In a further preferred embodiment, $R^3$—Z and independently $R^4$—Z are selected from ethyl-oxy-carbonyl, 2,3-dihydroxy-propyl-oxy-carbonyl, and H(OCH$_2$CH$_2$)$_5$—O—C(=O)—. Preferably, $R^3$—Z and $R^4$—Z are the same. Particularly preferred is that $R^3$—Z and/or $R^4$—Z is/are ethyl-oxy-carbonyl.

Particularly preferred crown ethers of the invention are shown below.

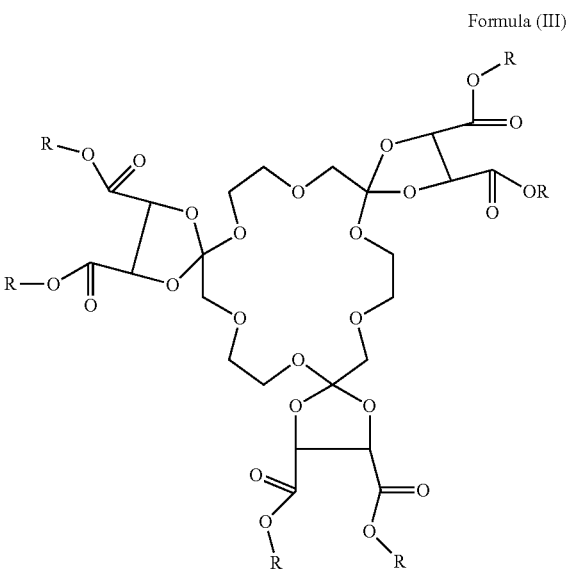

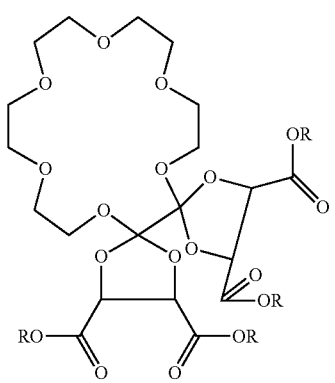
Formula (VI)
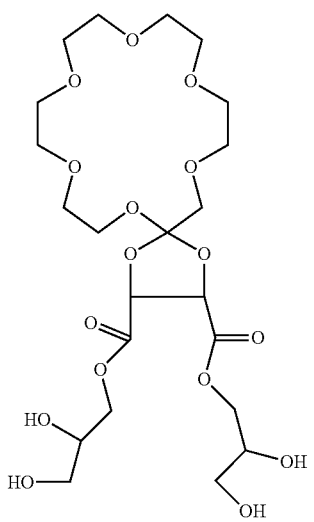
Formula (IX)
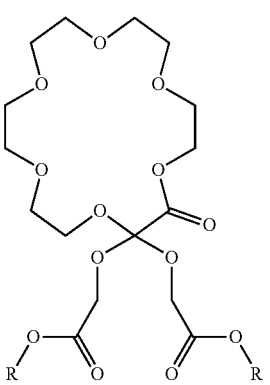
Formula (VII)
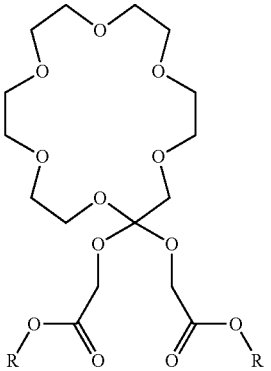
Formula (X)
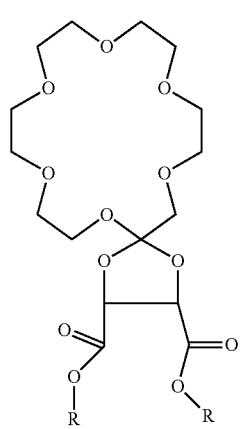
Formula (VIII)
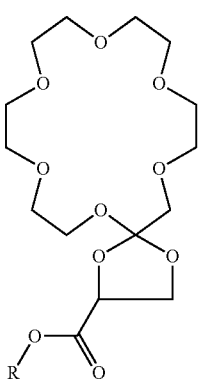
Formula (XI)

Formula (XII)

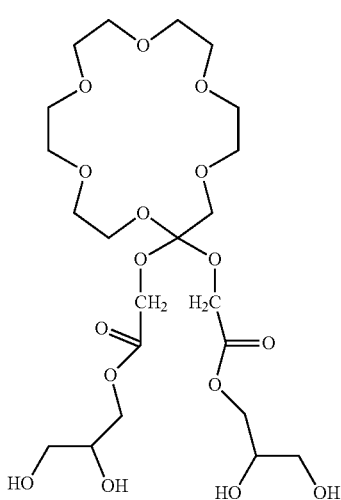

wherein R, independently for each occurrence, is selected from hydrogen; linear or branched and substituted or unsubstituted $C_1$ to $C_{10}$ alkyl, alkenyl and alkinyl; substituted or unsubstituted aryl with up to 10 ring atoms; and $H(OCH_2CH_2)_k$—, wherein k is an integer number from 1 to 10; wherein substituents, if present, are selected from OH and halogen.

In preferred embodiments, R, independently for each occurrence, is selected from hydrogen, methyl, ethyl, n-propyl, i-propyl and ($H(OCH_2CH_2)_5$—). Particularly preferred is that R is ethyl.

Furthermore it is preferred that in embodiments with more than one occurrence of R, all occurrences of R are selected to be the same.

In case of formula (VII), a particularly preferred group R is ethyl.

The present invention also relates to a composition comprising one or more crown ethers as defined herein.

A preferred composition (for further details on compositions see below) comprising crown ethers according to the invention is mildly acidic, preferably having a pH in the range from about 3 to 5, more preferably from about 3.5 to 4.

As stated further below, provided is also a pharmaceutical or diagnostic composition comprising one or more crown ethers according to the invention and a pharmaceutically or diagnostically active agent as defined further below. A preferred example of such active agent is a peptide. For peptides that are not soluble and/or not stable under acid pH below 6.50, preferred compositions are non-ionic. Preferably such non-ionic composition comprises or consists of, in addition to one or more peptides as defined above, mono acyl glycerols, a neutral organic solvent (i.e., not acid and not basic) and optionally a non ionic surfactant.

Preferably such composition further comprises lipids. Of particular interest are lipids where a lipid molecule comprises one or more fatty acid moieties. Examples of such lipids are triacylglycerols, diacylglycerols, monoacylglycerols and phospholipids. Preferred fatty acids are permeability-enhancing fatty acids such as aliphatic carboxylic acids, which may be saturated or unsaturated, branched or linear. Also envisaged is the presence of different fatty acid moieties within a lipid molecule comprising more than one fatty acid moiety. Moreover, mixtures of different lipids are envisaged as constituents of the above defined composition. Examples of fatty acids of particular interest include saturated fatty acids having 7-19 carbon atoms, preferably selected from caprylic acid, octanoic acid, nonanoic acid, decanoic acid, undecanoic acid, dodecanoic acid, myristic acid, palmitic acid, stearic acid, and arachidic acid. Examples of unsaturated fatty acids include those having 7-19 carbon atoms, preferably selected from palmitoleic acid, oleic acid, linoleic acid, and alpha-linoleic acid.

Additional preferred lipids are castor oil (Cremophor EL, d-α-tocopherol (Vitamin E), Beta carotene and Vitamin A.

A preferred formulation is where the non-aqueous hydrophobic vehicle comprises at least one acylglycerol, at least one lipid, and optionally, at least one organic solvent, such as a water soluble organic solvent. Another preferred formulation is where the non-aqueous hydrophobic vehicle comprises at least one acylglycerol, at least one water soluble organic solvent, optionally a non-ionic surfactant, and optionally one lipid.

In a further preferred embodiment, the active agent according to the invention, preferably a peptide, may be formulated only with one or more crown ethers of the invention. In other words, pharmaceutical and diagnostic compositions are provided which preferably consist of one or more active agents, preferably one or more peptides, and one or more crown ethers of the invention. In such embodiments, the crown ether may also function as vehicle.

Examples of the non-ionic surfactant include, but are not limited to, polyoxyl 35, polyoxyl 40 hydrogenated castor oil (Cremophor RH 40), and polyoxyl 60 hydrogenated castor oil (Cremophor RH 60), as well as d-α-tocopherol, polyethylene glycol 1000 succinate, polysorbate 20, polysorbate 80, Sorbitan-monolaurate (Span 20), Sorbitan monopalmitate (Span 40); Sorbitan monostearate (Span 60); Sorbitan-monooleate (Span 80), Solutol HS 15, sorbitan monooleate, poloxamer 407, Labrafil M-1944CS, Labrafil M-2125CS, Labrasol, Gellucire 44/1.

A further preferred formulation is where the lipid is a fatty acid. Preferred fatty acids are given above. Under such conditions, the presence of one or two electron-withdrawings group Z in the orthoester has a stabilizing effect on the crown ether of the invention. A preferred composition is a pharmaceutical or diagnostic composition as further detailed below.

Under conditions which are about pH-neutral, including physiological conditions, the crown ethers according to the invention are more labile. Generally speaking, orthoesters are more stable at basic pH, with stability decreasing towards neutral pH. When one or more Z groups are present, the Z group being an ester with the carbonyl group being directly bound to the cyclic structure of formula (II), the ester will be cleaved at neutral pH and under physiological conditions, thereby triggering elimination of the orthoester bearing the Z group. Lability of the crown ethers of the invention under physiological conditions is desirable, noting that upon delivery of a pharmaceutically or diagnostically active agent complexed with one or more crown ethers of the invention, said crown ethers are generally not needed any more and their degradation is preferred.

Physiological conditions in accordance with the present invention may vary significantly, for example when comparing the interior of a cell to the extracellular space. Exemplary intracellular conditions comprise 14 mM $Na^+$, 140 mM $K^+$, $10^{-7}$ mM $Ca^{2+}$, 20 mM $Mg^{2+}$, 4 mM $Cl^-$, 10 mM $HCO_3^-$, 11 mM $HPO_4^{2-}$ and $H_2PO_4^-$, 1 mM $SO_4^{2-}$, 45 mM phosphocreatine, 14 mM carnosine, 8 mM amino acids, 9 mM creatine, 1.5 mM lactate, 5 mM ATP, 3.7 mM hexose monophosphate, 4 mM protein and 4 mM urea. Exemplary interstitial conditions comprise 140 mM $Na^+$, 4 mM $K^+$, 1.2 mM $Ca^{2+}$, 0.7 mM $Mg^{2+}$, 108 mM $Cl^-$, 28.3 mM $HCO_3^-$, 2 mM $HPO_4^{2-}$ and $H_2PO_4^-$, 0.5 mM $SO_4^{2-}$, 2 mM amino acids, 0.2 mM creatine, 1.2 mM lactate, 5.6 mM glucose, 0.2 mM protein and 4 mM urea.

The present invention furthermore provides a pharmaceutical or diagnostic composition comprising one or more crown ethers according to the invention and a pharmaceutically or diagnostically active agent, said pharmaceutically or diagnostically active agent comprising one or more primary and/or secondary protonated amino groups and/or protonated guanidinium groups and/or said pharmaceutically or diagnostically active agent is a salt with a metal ion or with an ammonium ion ($NH_4^+$). The term "pharmaceutically active agent" refers to any agent capable of eliciting pharmaceutical effects. The term "drug" is used equivalently herein. A pharmaceutical composition according to the invention comprises one or more pharmaceutically active agents. It may also comprise more than one crown ether according to the invention.

Further preferred features and constituents of pharmaceutical and diagnostic compositions according to the invention are described herein above in conjunction with compositions according to the invention. In particular, mildly acidic compositions, preferably having a pH in the range from about 3 to 5, more preferably from about 3.5 to 4.

In said composition, (a) transmembrane and/or transmucosal delivery; (b) solubility in non-aqueous solvents; and/or (c) stability of said agent are improved owing to the presence of one or more crown ethers according to the invention. Accordingly, it is envisaged that, according to a preferred embodiment, said composition is confectioned for transdermal and/or transmucosal delivery.

The term "formulation" relates to the preparing or confectioning of a pharmaceutical or diagnostic composition.

The invention furthermore relates to the use of a crown ether according to the invention in the formulation of a pharmaceutically or diagnostically active agent, said active agent comprising one or more protonated primary and/or protonated secondary amino groups and/or protonated guanidinium groups and/or said pharmaceutically or diagnostically active agent is a salt with a metal ion or with an ammonium ion.

Also provided is a method of preparing a pharmaceutical or diagnostic composition comprising the step of bringing into contact a crown ether according to the invention with a pharmaceutically or diagnostically active agent, said agent comprising one or more primary and/or secondary protonated amino groups and/or protonated guanidinium groups and/or being a salt with a metal ion or with an ammonium ion.

"Bringing into contact" according to the invention is to be effected under conditions suitable for formation of a complex between the one or more primary and/or secondary protonated amino groups and/or protonated guanidinium groups with said crown ether.

Conditions suitable for complex formation include a solution of said pharmaceutically or diagnostically active agent and of said crown ether in a mixture of water and one or more organic solvents (e.g. a mixture of water, acetonitrile and alcohol), an organic solvent containing 1 to 10 vol.-% of water, or an organic solvent. Preferred organic solvents are polar and/or protic solvents such as methanol or ethanol. Alternatively, also apolar and aprotic solvents such as dichloromethane may be used. In a preferred embodiment of the method of the invention, said bringing into contact occurs in a solution of said pharmaceutically or diagnostically active agent and of said crown ether in a polar and/or protic solvent. In a further preferred embodiment, said polar and/or protic solvent is subsequently removed, for example by evaporation. In a more preferred embodiment, the complex obtained upon evaporation is taken up in an apolar solvent or a hydrophobic mixture, which preferably is a lipid mixture. The lipid mixture may include different lipids. As stated further above, the term "lipid" comprises but is not limited to a fatty acid. Preferred fatty acids are permeability-enhancing fatty acids such as aliphatic carboxylic acids, acyl-glycerols, and non-acid lipids such as vitamins A and E. The lipid mixture optionally contains an organic solvent. Preferred aliphatic carboxylic acids are defined further above. This two-step procedure of preparing a complex dissolved in an apolar and aprotic solvent may yield solutions of said active agent of higher concentration as compared to the "direct" procedure of combining active agent, crown ether, and apolar and aprotic solvent.

Preferably, said active agent is a peptide, a polypeptide, a protein, a small molecule, a saccharide, a polysaccharide or a nucleic acid, more preferably an RNAi agent.

The term "peptide" refers to a polymer of amino acids which consists of up to 30 amino acids. The term "polypeptide" refers to polymers of amino acids comprising more than 30 amino acids. The term "polypeptide" furthermore comprises proteins, as long as proteins consist of a single polypeptide. Proteins in general may also comprise more than one polypeptide chain. Also used herein is the term (poly)peptide. This term embraces both peptides and polypeptides.

The terms "peptide", "polypeptide" and "protein" include compounds which comprise one or more non-naturally occurring amino acids such as beta-alanine, alpha-amino butyric acid, gamma-amino butyric acid, alpha-amino isobutyric acid, norvaline, norleucine, epsilon-lysine, ornithine, homoserine and hydroxyproline. Furthermore, reactive groups including N- and C-terminus may be blocked by protection groups. Also further derivatizations of peptides, polypeptides and proteins as known in the art, including naturally occurring post-translational modifications, are deliberately included.

A "small molecule" has a molecular weight which is preferably below 1000, more preferably below 900, below 800, below 700 or below 600 g mol$^{-1}$. Preferred is also a molecular weight of about 500 or less. However, also active agents which not necessarily are biomolecules selected from peptides, polypeptides, proteins, saccharides and nucleic acids and having a molecular weight between 500 and 5000 g mol$^{-1}$ are envisaged.

The term "small molecule" comprises organic and inorganic small molecules.

A "small organic molecule" is a small molecule comprising a carbon skeleton and, optionally one or more heteroatoms, preferably selected from O, N, S and P.

It turns out that the advantageous effects of the crown ethers of the present invention, including improvement of transmembrane and/or transmucosal delivery, of solubility in non-aqueous solvents, and/or of stability of the active agents being complexed with a crown ether of the invention are not only observed with active agents which are small molecules, but also with active agents which are peptides, polypeptides or proteins. This is particularly surprising, since entirely different mechanisms or effects are responsible for said improvement in either case. In case of small molecules, complexation with crown ethers of the invention typically leads to a substantial shielding of said small molecule. This is because size-wise, it is a small molecule (the crown ether) complexing another small molecule (the pharmaceutically active agent). In addition, small molecules, due to their small size (for example in the range of 500 Dalton or less) can also be absorbed through a paracellular mechanism, i.e., through the small pores or channels between the cells composing the tissue. If furthermore the small molecule in matter possesses other specific features including a pronounced hydrophobicity, the molecule is absorbed via a transcellular pathway, i.e., by passive absorption, as well. In addition, it has to be understood that any properties, in particular physico-chemical properties of said small molecule, said properties comprising for example transmembrane and/or transmucosal delivery, become less relevant upon complexation, since complexation entails shielding of essentially the entire small molecule due to size similarity.

In case of biopolymers such as for example peptides, polypeptides, proteins, saccharides, polysaccharides and nucleic acids on the other hand, shielding of the entire molecule by the crown ether of the invention typically does not occur since in general the size of a polypeptide or protein will exceed significantly the size of said crown ether; nevertheless, said improvement does still occur. Surprisingly it turns out that unlike small molecules that are known to cross membranes, the local shielding of charges on said peptides, polypeptides or proteins, which on the contrary are known not to cross membranes, is sufficient to entail said improvement. A global shielding of the entire peptide, polypeptide or protein surprisingly turns out not to be the major driving force when said improvement is to be achieved.

In the embodiments described above, a mixture of crown ethers according to the invention may be used. Preferably, however, only one chemical species is used.

The capability of the crown ethers of the invention to form a complex with said protonated primary amino group or protonated secondary amino group or protonated guanidinium group can be verified in a straightforward manner by the skilled person.

A suitable assay comprises assessment of the solubility of an active agent such as a peptide or protein, for example insulin or erythropoietin, in organic solvent, for example methanol, ethanol or dichloromethan. In a first experiment, solubility of the peptide, polypeptide or protein in the organic solvent is determined. In a second experiment, a 1.1 to ten-fold molar excess, more preferably 1.5- to five-fold molar excess of a crown ether of the invention is added to the peptide or protein together with the organic solvent. The term "molar excess" refers to an amount of the crown ether which exceeds the amount of protonated primary amino groups, protonated secondary amino groups and protonated guanidinium groups of the peptide or protein or any positively charged moiety including organic and inorganic counter-ions at negatively charged carboxylates. In the absence of a crown ether of the invention, the peptide/protein generates a suspension, colloidal suspension or deposits in the form of particles.

In a further embodiment of the assay, any insoluble material still present in either experiment may be removed by centrifugation and the concentration of peptide/protein in solution subsequently determined by means known in the art. Such means include HPLC analysis of the supernatant from the centrifugation and determination of the amount of peptide or protein by determining the area of the peptide/protein peak in the chromatogram.

Preferably, the dissociation constant $K_D$ of said complex is less $10^{-3}$, more preferred less than $10^{-4}$, $10^{-5}$ or $10^{-6}$ mol$^{-1}$ l.

The term "metal ion" as used herein refers to any metal ion. Preferably it relates to ions of those metals which are present in the human body. Specific preferred metal ions include $Na^+$, $K^+$, $Ca^{2+}$, $Li^+$ and $Mg^{2+}$.

Preferably, said pharmaceutical or diagnostic composition is to be delivered in a non-invasive way such as orally, buccally, sublingually, nasally, pulmonary, dermally, transdermally, ocularly and/or rectally. The term "buccally" includes compositions which are absorbed in the mouth. As stated above, it is one of the advantages of the present invention that active agents which so far could only be delivered in an invasive manner can now, in view of the teaching of the present invention, be obtained in their complexed form with crown ethers of the invention and administered in a non-invasive manner. Also preferred, for the reasons stated above, is subcutaneous administration.

Preferred saccharides and polysaccharides are saccharides and polysaccharides having one or more sulfonic acid groups ($—SO_3^-$) such as heparin. Heparin is a heterogeneous group of straight-chain anionic mucopolysaccharides, called glycosaminoglycans having anticoagulant properties. Although others may be present, the main sugars occurring in heparin are: (1) α-L-iduronic acid 2-sulfate, (2) 2-deoxy-2-sulfamino-α-D-glucose 6-sulfate, (3) β-D-glucuronic acid, (4) 2-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. In heparin sodium, the acidic protons of the sulfate units are partially replaced by sodium ions. Shown below is a representative fragment of heparin Sodium:

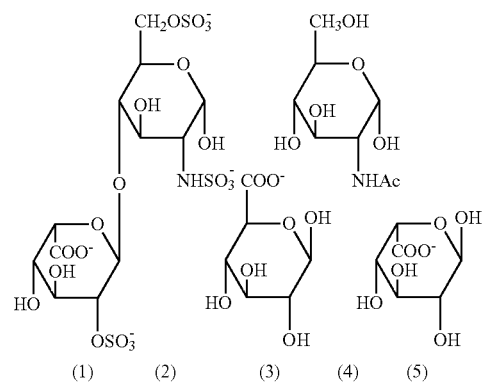

Heparin Sodium, and Heparin Calcium have been approved as medicaments. The uses of the present invention is expected to permit an enhancement of absorption, delivery and/or stability (half life) of Heparin Sodium and Heparin Calcium. The same is expected to apply to a lysine salt of heparin.

In case of pharmaceutically active agents being nucleic acids it is envisaged to use the crown ethers for the shielding of the positive charges of counterions of the negatively charged phosphates. Said (positively charged) counterions include ammonium, amino acids such as Lys and derivatives thereof, and metal ions. Also included are nucleic acids where the phosphate is esterified with an alkyl amino or alkyl guanidino group. Nucleic acids in accordance with the present invention, include DNA, such as cDNA or genomic DNA, and RNA. Furthermore, the term "nucleic acid" includes single-stranded and double-stranded oligonucleotides. It is understood that the term "RNA" as used herein comprises all forms of RNA including mRNA, ncRNA (non-coding RNA), tRNA and rRNA. The term "non-coding RNA" includes siRNA (small interfering RNA), miRNA (micro RNA), rasiRNA (repeat associated RNA), snoRNA (small nucleolar RNA), and snRNA (small nuclear RNA).

A preferred nucleic acid is an RNAi agent. RNAi agent are agents capable of triggering RNA interference. RNAi agents include small interfering RNAs. The term "small interfering RNA" (siRNA), sometimes known as short interfering RNA or silencing RNA, refers to a class of generally short and double-stranded RNA molecules that play a variety of roles in biology and, to an increasing extent, in treatment of a variety of diseases and conditions. Most notably, siRNA is involved in the RNA interference (RNAi) pathway where the siRNA interferes with the expression of a specific gene (see, e.g. Zamore Nat Struct Biol 2001, 8(9):746-50; Tuschl T. CHEMBIOCHEM. 2001, 2:239-245; Scherr and Eder, Cell Cycle. 2007 February; 6(4):444-9; Leung and Whittaker, Pharmacol Ther. 2005 August; 107(2):222-39; de Fougerolles et al., Nat. Rev. Drug Discov. 2007, 6: 443-453). Furthermore comprised are double-stranded ribonucleic acids which, upon processing within a cell or organism, for example by the enzyme Dicer, give rise to siRNAs.

Preferred polypeptides or proteins are antibodies. The term "antibody" includes monoclonal antibodies, polyclonal antibodies, single chain antibodies, or fragments thereof, also including bispecific antibodies, synthetic antibodies, antibody fragments, such as Fab, a F(ab$_2$)', Fv or scFv fragments etc., or a chemically modified derivative of any of these. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity.

The term "scFv fragment" (single-chain Fv fragment) is well understood in the art and preferred due to its small size and the possibility to easily produce such fragments by recombinant means.

In a particularly preferred embodiment of the use or the method of the invention, said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A10 239 400 and WO90/07861.

The terms "small molecule" or, where applicable, "small organic molecule" as used herein include the agents listed in the following, wherein the corresponding medical indication is also provided: (a) Synthetic and natural Antibiotics: derivatives of Pyridonic ring (Nalidixix acid, Oxolinic acid), Penicillin derivatives (Benzyl-Penicillin, Phenoxymethyl-penicillin, Meticillin, Oxacillin, Ampicillin, Amoxycillin, Pivampicillin, Talampicillin, Carbenicillin, Ticarcillin), Cefalosporin derivatives (Cefalosporin C, Cefaloglycine, Cefotaxime, Cefinetazole, Cefradin, Cefalexin, Cefalotin, Cefaloridin, Cefazolin, Cefsulodin, Cefacetril, Cefapyrin, Cefuroxime, Cefamandol, Cefoxitin, Cefazol Cefoperazone, Ceftriaxone), aminoglycoside antibiotics (Streptomycin, Neomycin, Gentamicin, Tobramycin, Amikacin), Polyenes (Nistatin, Amphotericin B), Anti-Tubercolosis (Para-amino salicylic acid) (b) Neuro-transmitters: Catecholamines (Adrenaline, Noradrenaline, L-Dopamine LevoDopa, Malevodopa (Levodopa methyl ester and analogs of thereof), Dopamine, Carbidopa, Serotonin, γ-amino-butyric acid (GABA); (c) Anti-inflammatory and Analgesic non steroids: Salicylic Acid, Acethylsalicylic acid; Phenylacetic acids: Ibuprofen, Phenoxyprofen, Ketoprofen, Naproxen, Diclofenac; Etherocyclic acetic acids: Indomethacine, Clometacine, Sulindac, Zomepirac, Thiapropheic acid; Antranilic acids: Mephenamic acid, Fluphenamic acid, Meclophenamic acid, Tolphenamic acid, Niflumic acid. (d) Anti-coagulants: Heparin (either sodium or calcium derivatives), Dermatan Sulfate, Enoxaparin Sodium, Dalteparin Sodium.; (e) Diuretics: Furosemide, Bumetanide, Etacrinic acid, Tienilic acid, Triamterene, Amiloride,; (e) Various: Valproic acid (anti-epilectic), Clavulanic acid (inhibitor of β-Lactamases), Lithium salts (anti-Psychotic).

It is understood that the invention also relates to further therapeutically relevant small molecules which are modified according to uses and methods of the invention, i.e. by complex formation. In this case, the envisaged medical indication is the indication which can be prevented, ameliorated or cured with the small molecule under consideration.

The term "peptide" according to the present invention and associated diseases to be treated include: (a) the peptide is Lisinopril also known as Privinil and the disease is hypertension; (b) the peptide is Goserelin, synthetic decapeptide analogue of luteinizing hormone-releasing hormone (LHRH) and the disease is Prostate Cancer; (c) the peptide is Calcitonin and the disease is Osteoporosis; (d) the peptide is Leuprolide and the disease is Prostate Cancer; (e) the peptide is Glucagon the disease is hypoglycemia; (f) the peptide is Integrilin the disease is Anti-coagulation; (g) the peptide is hirudin and is used as anticoagulant and antithrombotic agent, (h) the peptide is desmopressin, which is an analogue of vasopressin and is used therapeutically as an antidiuretic and in the management of bleeding in individuals with some forms of hemophilia and von Willebrand's disease, and wherein the (poly)peptide is modified as defined herein above, i.e. by formation of a complex with cyclic compounds of the invention.

It is understood that the invention also relates to the use of further therapeutically relevant peptides which are modified (i.e. complexed) according to the invention. In this case, the envisaged medical indication is the indication which can be prevented, ameliorated or cured with the peptide or polypeptide under consideration.

The term "(poly)peptide" according to the present invention and associated diseases to be treated include: (a) the (poly)peptide is insulin (Including Insulin Lispro, insulin aspart, and the disease is diabetes; (b) the (poly)peptide is Epoietin alpha and the disease is anemia; (c) the (poly)peptide is Epoietin beta and the disease is anemia; (d) the (poly) peptide is darbepoetin and the disease is anemia; (e) the (poly)peptide is Erythropoietin and the disease is anemia or chronic renal failure; (f) the (poly)peptide is Filgrastim and the indications are Immune disorders, leukemia, diabetic foot ulcers; Leukopenia, and neoplastic diseases; (g) the (poly) peptide is Lenograstim and the indication is Leukopenia; (h) the (poly)peptide is Sargramostin and the indication is Leukopenia; (i) the (poly)peptide is Molgramostin and the indication is Leukopenia; (j) the (poly)peptide is Mirimostim and the indication is Leukopenia; (k) the (poly)peptide is Nartograstim and the indication is Leukopenia; (l) the (poly) peptide is GCSF and the disease is Chemotherapy induced neutropenia; (m) the (poly)peptide is GMCSF and the indication is Autologous bone marrow transplant; (n) the (poly) peptide is an asparaginase and the disease is cancer; Preferred cancer forms amenable to treatment with asparaginases are lymphoblastic leukemias and large cell lymphoma; (O) the (poly)peptide is Factor VIIa, Factor VIII, Factor IX products (Blood clotting factors) and the disease are Hemophilia A, Hemophilia b; (p) the (poly)peptide is interferon α-alpha- (includes interferon alpha-2a, interferon alpha-2b, interferon alfacon-1, interferon alpha 3n) and the disease is chronic hepatitis B or C and some types of cancer; (q) the (poly) peptide is interferon β (wherein -beta- includes Interferon beta-1a, and interferon beta 1b) to treat Multiple Sclerosis and hepatitis; (r) the (poly)peptide is interferon γ (wherein -gamma- includes Interferon gamma-1b) and the disease is fibrosis, tuberculosis, meningitis or cancer; (s) the (poly) peptide is human growth hormone (hGH) and the disease is Human growth deficiency in children; (t) the (poly)peptide is somatrem/somatropin and the disease is growth hormone deficiency in children; (u) the (poly)peptide is a superoxide dismutase and the disease is a brain injury; (v) the (poly) peptide is interleukine-2 and the disease is cancer (metastatic renal cancer) or a condition requiring immunostimulation; (w) The human growth hormone (hGH) antagonist B2036 is well known in the art. B2036 is obtained from hGH by the introduction of nine amino acid replacements conferring antagonistic properties and increased receptor affinity (see U.S. Pat. No. 5,849,535). For the purpose of treating acromegaly any other growth hormone (GH)-receptor antagonist (alternatively or in addition to the GH-receptor antagonist 82036) is envisaged; (x) the (poly)peptide is Transtuzumab and the disease is Cancer; (y) the (poly)peptide is exendin-4 and the disease is diabetes II or obesity; (z) the peptide is PTH 1-34 (teriparatide) and the disease is osteoporosis; (aa) the peptide is Taspoglutide and the disease is diabetes II or obesity; (bb) the peptide is Liraglutide and the disease is diabetes II or obesity; (cc) the peptide is Albiglutide and the disease is diabetes II or obesity; (dd) the peptide is Taspoglutide and the disease is diabetes II or obesity; (ee) the peptide is ZP10 (AVE0010) and the disease is diabetes II or obesity; (ff) the peptide is OP-286 and the disease is diabetes II or obesity. It is understood that the term (poly)peptide as used herein includes peptides, polypeptides and proteins.

It is understood that the invention also relates to the use of further therapeutically relevant (poly)peptides which are modified (i.e complexed) according to the invention. In this case, the envisaged medical indication is the indication which can be prevented, ameliorated or cured with the (poly)peptide under consideration.

The term "diagnostically active agent" refers to any agent suitable for practising a method of diagnosis. Examples include peptides, polypeptides, antibodies or small organic molecules which bind a target molecule the presence, absence and/or amount of which is to be determined. The target molecule in turn may be any molecule occurring in the human or animal body in a healthy and/or diseased state. The term "target molecule" includes peptides, polypeptides and proteins. Preferably, said diagnostically active agent is detectably labelled.

The pharmaceutically or diagnostically active agent according to the invention exhibits one or more groups selected from protonated primary amino groups ($-NH_3^+$), protonated secondary amino groups ($-NH_2^+-$) and protonated guanidinium groups ($-NH-C(=NH_2^+)-NH_2$). The presence of one or more positive charges limits the possibilities to formulate and deliver said agent in the absence of crown ethers of the invention. In a preferred embodiment, said primary or said secondary amino group is a primary or secondary aliphatic amino group, respectively. Also, said guanidinium group is preferably an aliphatic guanidinium group, i.e., a guanidinium group attached to an aliphatic moiety. In those cases where said active agent is a peptide, polypeptide, protein or antibody, it is understood that "primary aliphatic amino group" includes or refers to the amino group of Lys, "aliphatic guanidinium group" includes or refers to the guanidinium group of Arg and "secondary amino group" refers to His and Trp.

In addition to pharmaceutically or diagnostically active agents, constituents of functional food or food supplements may be complexed with the compounds of the invention, provided that the constituent of a functional food or the constituent of a food supplement carries one or more of protonated primary amino groups, protonated secondary amino groups and protonated guanidinium groups and/or is a salt with a metal ion. Such constituent (also referred to as active agent) may take the place of the pharmaceutically or diagnostically active agents in the uses and methods of the invention. An example of a constituents of functional food is creatine.

Accordingly, the present invention also relates to use of a crown ether of the invention; wherein said crown ether is capable of forming a complex with a protonated primary and/or protonated secondary amino group and/or a protonated guanidinium group and/or with a salt with a metal ion for improving (a) transmembrane and/or transmucosal delivery; (b) solubility in non-aqueous solvents; and/or (c) stability of an active agent, wherein said active agent comprises one or more protonated primary and/or protonated secondary amino groups and/or a protonated guanidinium groups. The term active agent comprises pharmaceutically active agents or drugs, diagnostically active agents as well as constituents of functional food and constituents of food supplements.

Pharmaceutical compositions according to the invention may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Preferred carriers for transmembrane or transmucosal delivery or diluents for formulation according to the invention include the non-aqueous solvents further discussed below. Compositions comprising such carriers can be formulated by well known conventional methods. These pharmaceutical compositions can be administered to the subject at a suitable dose. The dosage regimen will be determined by the attending physician and depending on clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. Envisaged formulations furthermore comprise microspheres, liposomes, microcapsules, and nanoparticles or nanocapsules.

To explain further, the increase of hydrophobicity by the shielding of the positive charge(s) present on the pharmaceutically or diagnostically active agent according to the compositions, uses and methods of the present invention opens possibilities to design novel delivery approaches: for example, entrapping the active ingredient into (i) liposomes, (ii) microspheres, (iii) microcapsules, (iv) nanoparticles/nanocapsules composed of, for example, but not limited to, polyacrylic acids (PAA), polymethacrylic acids (PMAA), polylactic and glycolic acids (PLGA), gabexate mesylate (GM), chitosan, starch, Terephthaloyl chloride (TC), crosslinked cyclodextrines, poly(ethylcyanoacrilate) (PECA), PEGs, and the like.

Additional envisaged constituents of the pharmaceutical or diagnostic compositions according to the invention include cyclodextrins (see, for example, Irie and Uekama (1999) or Challa et al. (2005)) and/or chitosan. Compositions comprising cyclodextrins or chitosan may exhibit retard characteristics, i.e., they provide for a delayed release and/or a release over an extended period of time of the active agent. Cyclodextrins form inclusion complexes with hydrophobic moieties present on a compound. Cyclodextrines are known to have lipophilic inner cavities and hydrophilic outer surfaces and are capable of interacting with a large number of molecules. Cyclodextrines are used in formulation to improve apparent drug solubility of hydrophobic (poorly water-soluble) drugs and thus enhance the bioavailability of insoluble drugs by increasing drug solubility, dissolution, and or drug permeability. In the context of the present invention, the enhanced hydrophobicity of the active agent due to the shielding of the positive charge(s) by crown ethers of the invention allows more direct and deeper incorporation into the lipophilic core of the cyclodextrine structure. In other words, a hydrophilic active agent being non covalently and temporarily complexed with compounds of the invention changes its biophysical properties and becomes hydrophobic such that it—or hydrophobic parts of if—can insert into the inner part (lipophilic core) of cyclodextrins. As a result, the active agent may be complexed first with cyclic compounds of the invention that shield the positive charge(s) present and then, in a second step, the complex formed by the active agent and said cyclic compound(s) may be allowed to form a complex with one or more cyclodextrins, thereby yielding in total two layers of complexation. The double complex is expected to be suitable for non-invasive drug delivery, including ocular, rectal, dermal and transdermal delivery, furthermore in parenteral drug delivery (injections), to target brain delivery by enhancing blood-brain barrier (BBB) passage, and in controlled drug delivery to act as functional carrier materials in pharmaceutical formulation to obtain efficient and precise delivery.

Accordingly, in another preferred embodiment, said pharmaceutical or diagnostic composition to be manufactured further comprises one or more cyclodextrins. Cyclodextrins are known in the art and include alpha-cyclodextrin, beta-cyclodextrin and gamma-cyclodextrin. Also this approach opens possibilities to design novel delivery approaches: for examples, entrapping the active ingredient into (i) liposomes, (ii) microspheres, (iii) microcapsules, (iv) nanoparticles/nanocapsules.

Furthermore, complexation of pharmaceutically active ingredients with crown ethers of the invention provides significant advantages in the field of galenics and pharmaceutical techniques. Indeed, especially in the case of biopolymers like for example peptides, polypeptides, proteins and nucleic acids that can be handled mainly in aqueous media, the dual and concomitant option of having a pharmaceutical ingredient be soluble both in water as well as in organic solvents (as a complex with crown ethers of the invention) may allow improved galenic forms including but not limited to: pills, tablets, capsules, suppository, elisirs, aereosols, drops, powders, lyophilized, emulsions, gels, creams, patches and colloids it has to be understood that improvement of galenic forms of said active agent is not an obvious consequence of or extrapolation from an improvement of transmembrane or transmucosal delivery. Crown ethers according to the invention lead to a increase of the hydrophobicity of a pharmaceutically or diagnostically active agent upon complexation with the cyclic compound. Concomitantly, a shielding of the positive charge of the protonated primary or secondary amino group or protonated guanidinium group occurs. The increase of hydrophobicity and the shielding of the positive charge(s) present on the pharmaceutically or diagnostically active agent opens previously unavailable possibilities for formulation. For example, predominantly hydrophilic active agents such as peptides, polypeptides or proteins including antibodies may be dissolved (in their complexed form) in solvents where their solubility in their uncomplexed form is low or zero. Such solvents include non-aqueous solvents. Furthermore, the increased hydrophobicity of the active agent in its complexed form opens new routes of administration for active agents which up to now could only be administered in an invasive manner such as intravenously. Despite such invasive administration (including intravenous administration) exhibits known disadvantages such as partial or significant degradation of the active agent in the liver, no other options have been available so far for a number of active agents including in particular proteinaceous active agents. Upon complexation with crown ethers according to the invention the active agent is rendered sufficiently hydrophobic to ensure sufficient permeation through cell membranes such as the cell membranes present in the mucosa or the skin. As a consequence, non-invasive delivery routes which are further detailed below can be considered for such active agents. Alternatively, non-invasive delivery may be an option also for the uncomplexed form of the active agent, however, with the disadvantage of limited permeation of the mucosa or the skin. In such a case, complexation with the crown ethers according to the invention enhances delivery and renders non-invasive delivery the preferred route of delivery. The pharmaceutical or diagnostic compositions obtained according to the use of the invention are preferably hydrophobic, noting that the hydrophobic complex of the active agent permits use of hydrophobic carriers. Owing to the hydrophobicity (and lipophilicity) of the composition, release of the active agent upon delivery to the subject may be retarded as compared to a conventional, less hydrophobic formulation. In other words, certain compositions obtained according to the invention are retard forms of the comprised active agent.

A further advantage of the present invention relates to invasive delivery, in particular to subcutaneous delivery. The volume of a pharmaceutical or diagnostic composition for subcutaneous delivery is inherently limited. If conventional formulation does not allow to obtain a solution for injection, wherein the limited volume for subcutaneous injection comprises the required dose, treatment is cumbersome (short intervals between administrations) or impossible. Noting that the uses of the invention permit preparation of compositions with elevated concentrations of the active agent, these problems in the prior art may be overcome.

In a preferred embodiment, the crown ether of the invention has a logP value which is greater than 1, more preferred greater than 2 and yet more preferred greater than 3.

The terms "hydrophobic" and "hydrophobicity" are well known in the art and designate a low or none miscibility with water and aqueous media. The terms "lipophilic" and "lipophilicity" are used with equivalent meaning herein. A parameter commonly used to quantify hydrophobicity is the logP value.

The mass flux of a molecule at the interface of two immiscible or substantially immiscible solvents is governed by its lipophilicity. The more lipophilic a molecule is, the more soluble it is in the lipophilic organic phase. The partition coefficient of a molecule that is observed between water and n-octanol has been adopted as the standard measure of lipophilicity. The partition coefficient P of a species A is defined as the ratio $P=[A]_{n\text{-}octanol}/[A]_{water}$. A figure commonly reported is the logP value, which is the logarithm of the partition coefficient. In case a molecule is ionizable, a plurality of distinct microspecies (ionized and not ionized forms of the molecule) will in principle be present in both phases. The quantity describing the overall lipophilicity of an ionizable species is the distribution coefficient D, defined as the ratio D=[sum of the concentrations of all microspecies]$_{n\text{-}octanol}$/[sum of the concentrations of all microspecies]$_{water}$. Analogous to logP, frequently the logarithm of the distribution coefficient, logD, is reported.

If the lipophilic character of a substituent on a first molecule is to be assessed and/or to be determined quantitatively, one may assess a second molecule corresponding to that substituent, wherein said second molecule is obtained, for example, by breaking the bond connecting said substituent to the remainder of the first molecule and connecting (the) free valence(s) obtained thereby to hydrogen(s). Alternatively, the contribution of the substituent to the logP of a molecule may be determined. The contribution $\pi_X$ of a substituent X to the logP of a molecule R—X is defined as $\pi_X=\log P_{R\text{-}X}-\log P_{R\text{-}H}$, wherein R—H is the unsubstituted parent compound.

Values of P and D greater than one as well as logP, logD and $\pi_X$ values greater than zero indicate lipophilic/hydrophobic character, whereas values of P and D smaller than one as well as logP, logD and $\pi_X$ values smaller than zero indicate hydrophilic character of the respective molecules or substituents.

The above described parameters characterizing the lipophilicity of the lipophilic group according to the invention can be determined by experimental means and/or predicted by computational methods known in the art (see for example Sangster, Octanol-water Partition Coefficients: fundamentals and physical chemistry, John Wiley & Sons, Chichester (1997)).

In practice, logP, logD and $\pi_X$ values will vary to a certain extent according to the specific conditions under which they are measured.

It has been shown that for drugs or active agents to have a reasonable probability of being well absorbed their logP value must not be greater than 5. The probability density of logP values of drugs on the market (see, for example, http://www.organic-chemistry.org/prog/peo/cLogP.html) shows a maximum at a logP value around 3.

In a further preferred embodiment of the uses and methods of the invention, the complex formation of said crown ether with said primary and/or secondary protonated amino group and/or protonated guanidinium group is selective. Selectivity can be assessed by the skilled person in a straightforward manner. To this end, a candidate ligand and a crown ether of the invention are brought into contact under conditions allowing formation of a complex. Complexed and/or free forms of ligand and/or cyclic compound are determined with any suitable means. Such assays are performed repeatedly (or in parallel), wherein one implementation of the assay is directed to determining the complex formation of said compound with said primary and/or secondary protonated amino group and/or protonated guanidinium group and at least one further implementation of the assay is directed to determining the complex formation of said compound with a competing species. Competing species include metal ions such K$^+$ and Na$^+$. Selectivity means that a majority of said compounds forms a complex with said primary and/or secondary protonated amino group and/or protonated guanidinium group ("complex A"; wherein "complex A" designates the amount or concentration of the complex formed between said cyclic compound on the one side and said primary and/or secondary protonated amino group and/or protonated guanidinium group on the other side), whereas the remainder (or a fraction of the remainder) forms a complex with one or more competing species ("complex B"; wherein "complex B" designates the sum of the amounts or concentrations of the complexes with the competing species). In other words, the ratio complex A/complex B is greater than 1. Preferably, said ratio is 1,2; 1,5; 2; 3; 4; 5; 10; 100, 1000 or more.

In a further preferred embodiment of the uses and methods of the invention, a counter ion is added to the composition. Preferred counter ions for a pharmaceutically or diagnostically active agent comprising one or more protonated primary and/or secondary amino groups and/or one or more protonated guanidinium groups, in particular for peptides, polypeptides and proteins, include trifluouracetate (TFA) and salts of alkanoic acids, preferably of alkanoic acids having between 2 and 30, more preferred between 2 and 20, yet more preferred between 2 and 10 carbon atoms. In other preferred embodiments such counter ion may comprise an aromatic group. These counter ions may be used to replace other counter ions forming a salt with said primary and/or secondary protonated amino group and/or protonated guanidinium group. Salts of alkanoic acids are more lipophilic than the generally occurring counter ions such as phosphate. TFA furthermore exhibits a lower pKa value, the consequence being a stronger salt link between the primary or secondary protonated amino group or protonated guanidinium group on the one side and TFA on the other side. Aryl carboxylates, such as benzoate and salycilate are further examples of suitable counterions. Another preferred class of counter ions in particular for peptides, polypeptides and proteins are alkyl or aryl sulfonic acids. Preferred alkyl sulfonic acids have an alkyl chain with between 1 and 30, more preferred between 8 and 10 carbon atoms. Aryl sulfonic acids with one or more alkyl substituents on the aromatic ring, each alkyl substituent preferably having between 2 and 30, more preferred between 8 and 10 carbon atoms, are further examples of suitable counterions. Examples are methanesulfonic acid (Mesylate counter ion) and p-toluensulfonic acid (Tosylate counter ion). Another class of preferred counter ions, in particular for peptides, polypeptides and proteins, are phospholipids with at least an acidic proton on the phosphate, such as a phosphatidyl glycerol or phosphatidyl sugar with one acidic proton, or a phosphatidic acid with two acidic protons. The alkanoic acids comprised in said phospholipids or the phosphatidyl moieties, respectively, preferably have between 4 and 30 each, more preferred between 6 and 20, yet more preferred between 8 and 18 carbon atoms. Phospholipids comprising two alkanoic acids may either symmetric or asymmetric. In the latter case, a phospholipid molecule comprises two different fatty acids. In another preferred embodiment, the phospholipids are of natural origin, like for example phosphatidylinositol.

On the other hand, preferred counter ions for acidic polymers (for example heparin) or other acidic pharmaceutically or diagnostically active agents are phospholipids that carry a positive charge. Preferably they have a free primary amino group like. Examples include, but are not limited to phosphatidyl serine and phosphatidyl ethanolamine.

An increased lipophilicity of the counter ion increases the stability of the complex between a cyclic compound of the invention with said primary and/or secondary protonated amino group and/or protonated guanidinium group.

Examples of pharmaceutically active agents which are salts comprising a primary or secondary amine are ibuprofen lysinate, i.e., the lysine salt of ibuprofen, and procaine penicillin. In case of ibuprofen lysinate, ibuprofen is the component of said salt providing a carboxylate and lysine is the component providing a primary amino group. Similarly, in case of procaine penicillin, penicillin is the component of said salt providing a carboxylate and procaine is the component providing a primary and a secondary amino group. While these are just specific examples, it is envisaged that any drug which (i) comprises a carboxylic acid functional group and (ii) is a salt with a compound comprising a primary or secondary amine or a guanidinium group may be formulated as a complex with a compound of the invention. Such drugs include anti-inflammatory drugs fulfilling these two requirements including ibuprofen lysinate as well as antibiotics such as procaine penicillin or aminoglycosides.

In a preferred embodiment of the uses and methods of the invention, said active agent being a peptide, polypeptide or protein comprises one or more amino acids selected from Asp and Glu.

In a more preferred embodiment, said pharmaceutical or diagnostic composition is acidic. This embodiment is directed to active agents which in addition to protonated primary and/or protonated secondary amino groups and/or a protonated guanidinium groups comprise groups which are negatively charged at neutral pH such as the carboxylates of Asp and Glu in peptides, polypeptides and proteins. In such a case, the aim of forming a complex with compounds of the invention, which is increasing hydrophobicity and shielding of charges might be more difficult to achieve, given the presence of said groups which are negatively charged at neutral pH such as the carboxylates of Asp and Glu. One option of removing the charges to acidify the composition to a pH where a significant fraction of said groups which are negatively charged at neutral pH become protonated and in consequence uncharged.

More preferred, said pharmaceutical or diagnostic composition has a pH-value between 2 and 6. Yet more preferred, the pH-value is between about 3 and about 5. Even more preferred is a pH-value between 3.5 and 4.

Alternative to said pharmaceutical or diagnostic composition being acidic or in addition thereto, one or more of the Asp or Glu residues are esterified with an amino alcohol and/or guanidinium alcohol, wherein the amino group of said amino alcohol is a primary or secondary amino group. Preferably, the majority (i.e. more than 50%), more preferred 60%, 70%, 80%, 90%, 95%, 98%, 99% or all of said Asp or Glu residues are esterified. The esterification leads to the formation of a prodrug. A "prodrug" is a compound that is generally not biologically and/or pharmacologically active. However, when activated, typically in vivo by enzymatic or hydrolytic cleavage to convert the prodrug to a biologically and/or pharmacologically compound, the administration of the prodrug will have the intended medical effect. Prodrugs are typically formed by chemical modification such as by the above described esterification of biologically and/or pharmacologically compounds. Conventional procedures for the selection and preparation of suitable prodrug derivatives are described, for example, in Design of Prodrugs, ed. H. Bundgaard, Elsevier, 1985.

Preferably, said amino alcohol is an omega-amino-alkyl-ol.

Preferably, said amino alcohol is 4-amino-1-butanol or 6-amino-1-hexanol. The esterified form of Asp and/or Glu is herein referred to as "pseudo-lysine", since a structure is generated which is similar to Lys in that a linear alkyl chain is bound with one of its termini to the carboxylate (via an ester bond), wherein the alkyl chain carries a primary amino group at the other terminus. Alternatively or in addition, omega-guanidinium-alcohols may used, thereby generating "pseudo-arginines", having a carbon chain between the guanidinium group and the ester function from 10 to 2 carbons, more preferably from 4 to 2. Optionally, the guanidinium group can be N-methylated at the nitrogen forming part of the secondary amine with said guanidinium group (as it is the case in creatine). In a further embodiment a polyol linker (1,1,1-Tris-(hydroxymethyl)ethane, glycerol or similar structure) may be used to attach two guanidinium groups to a single Asp or Glu residue. In the latter case, one hydroxyl group of the glycerol or polyol linker is esterified with the Asp or Glu side chain carboxylic acid, and the remaining hydroxyl moieties may be esterified with one two or more molecules of a guanidinium alcanoic acid.

Generally speaking, said active agent being a peptide, polypeptide or protein (a) may be esterified or thio-esterified (i) at the carboxylate of the C-terminus with a guanidinium alkanol, a guanidinium alkanethiol, a polyethylene glycol (PEG) substituted with a guanidinium group and having a free hydroxyl group, or a PEG substituted with a guanidinium group and a sulfhydryl group; (ii) at a side-chain carboxylate of one or more Asp or Glu residues, if present, with a guanidinium alkanol, a guanidinium alkanethiol, a PEG substituted with a guanidinium group and having a free hydroxyl group, or a PEG substituted with a guanidinium group and a sulfhydryl group; (iii) at a hydroxyl group of one or more Ser, Thr or Tyr residues, if present, with a guanidinium alkanoic acid or a PEG substituted with a guanidinium group and a carboxyl group; (iv) at a sulfhydryl group of one or more Cys residues, if present, with a guanidinium alkanoic acid or a PEG substituted with a guanidinium group and a carboxyl group; and/or (v) at the N-terminus with a guanidinium alkanoic acid or a PEG substituted with a guanidinium group and a carboxyl group, wherein said N-terminus is previously amidated with an alpha- or beta-hydroxy acid, and wherein the ester is formed between the hydroxy group of said alpha- or beta-hydroxy acid and the carboxylic group of said guanidinium alkanoic acid or said PEG substituted with a guanidinium group and a carboxyl group; and/or (b) may contain one or more disulfides, the disulfide being formed between the sulfhydryl group of a Cys reside, if present, and a guanidinium alkanethiol or a PEG substituted with a guanidinium group and a sulfhydryl group.

In a preferred embodiment, (i) an excess of said crown ether is used; and/or (ii) a second crown ether according to the invention is used, wherein said second crown ether preferably forms a complex with a cation, said cation being a counter ion of the carboxylate of said Asp and/or Glu. The term "cation" includes inorganic cations. Inorganic cations include metal ions such as $Na^+$ and $K^+$. Alternative to or in addition to the options of acidifying the composition, esterifying said Asp and/or Glu, this embodiment provides two further options. Any of these four options may be used alone or in combination.

Accordingly, in a further preferred embodiment of the method of preparing a pharmaceutical or diagnostic composition of the invention, said active agent is a peptide, polypeptide or protein comprising one or more amino acids selected from Asp and Glu and the method comprises the further step(s) of (b) acidifying said pharmaceutical or diagnostic composition; (c) esterifying one or more of the Asp or Glu residues with an amino alcohol, wherein the amino group of said amino alcohol is a primary amino group; and/or (d) bringing into contact with said pharmaceutically or diagnostically active agent one or more further compounds of the invention, wherein said further compound(s) preferably form(s) a complex with a metal ion, said metal ion being a counter ion of the carboxylate of said Asp and/or Glu.

The term "excess" relates to amounts of said compound which exceeds an equimolar amount of said primary and/or secondary amino groups and/or guanidinium groups to be complexed. Such excess may be used to ensure complexation of a substantial fraction or all of said primary and/or secondary amino groups and/or guanidinium groups to be complexed. While equimolar amounts may be sufficient to this end, it is preferred to use an excess such as a three- to ten-fold molar excess or more preferably three- to five-fold molar excess.

Any excess amount not involved in complexes with primary and/or secondary amino groups and/or guanidinium groups will be available for the complexation of cations which serve as counter ions of the negatively charged carboxylates present on said Asp and/or Glu residues. To ensure complexation of these counter ions as well (in addition to complexation of a substantial fraction or all of said primary and/or secondary amino groups and/or guanidinium groups), a preferred amount of crown ether of the invention is a five- to seven-fold molar excess of the amount of carboxylates. As a consequence, it is preferred to use an amount of said crown ether which is a sum of a three- to five-fold molar excess of the amount of primary and/or secondary amino groups and/or guanidinium groups and a five- to seven-fold molar excess of the amount of carboxylates. Such complexation of cations by crown ethers of the invention designed to complex primary and/or secondary amino groups and/or guanidinium groups will work the better the less specific the complexation of said primary and/or secondary amino groups and/or guanidinium groups is. In case crown ethers of the invention are used which complex said primary and/or secondary amino groups and/or guanidinium groups with a high degree of specificity, it is preferred to use a second crown ether of the invention, wherein said second crown ether preferably forms a complex with said cation, said cation being for example a metal ion. In those cases said compound which complex said primary and/or secondary amino groups and/or guanidinium groups are referred to as "first" compounds. In a further preferred embodiment, the first cyclic compound and/or the second cyclic compound are capable of forming a complex with an ammonium ion ($NH_4^+$).

The Examples illustrate the invention.

EXAMPLE 1

Synthesis of Compounds According to the Invention

A synthetic pathway to compounds of the invention is depicted in scheme 1. Protected HEAA derivatives 3 and 10 were prepared respectively starting from 2-(tetrahydro-2H-pyran-2-yloxy)ethanol 1 (commercially available or obtained from THP selective monoprotection of diethylene glycol) and commercially available 2-(benzyloxy)ethanol 8. Fully protected 3 was obtained by a two steps procedure including formation of acid 2 by reaction of alcohol 1 with bromoacetic acid, followed by DIC/DMAP promoted coupling with benzyl alcohol. Further removal of THP protecting group afforded alcohol 4 which was coupled with acid 2 to give dimer 5 with 82% yield. Final deprotection by acidic treatment led to the obtention of desired alcohol 6, first building block for key trimer compound 11 obtention. This conversion also led to the formation of small amounts of alcohol 7, thus reflecting the instability of this latter in these conditions (probable intramolecular transesterification of the dimer alcohol 6). Attempts to obtain pure dimer 6 by flash chromatography gave only poor yields and crude residue was finally used for next step without further purification.

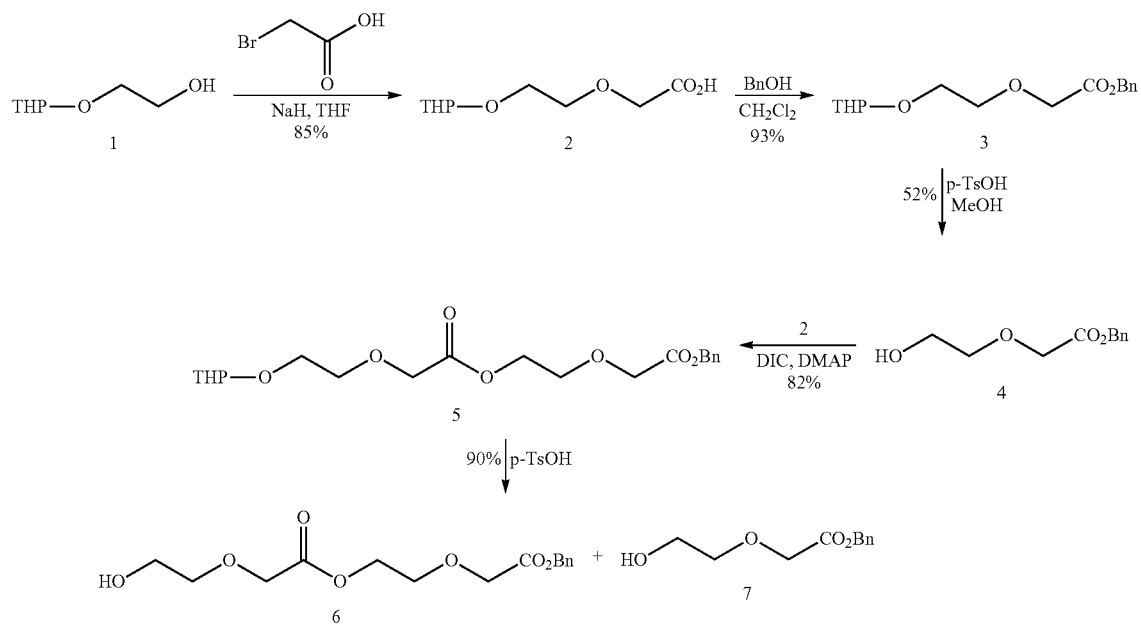

Scheme 1

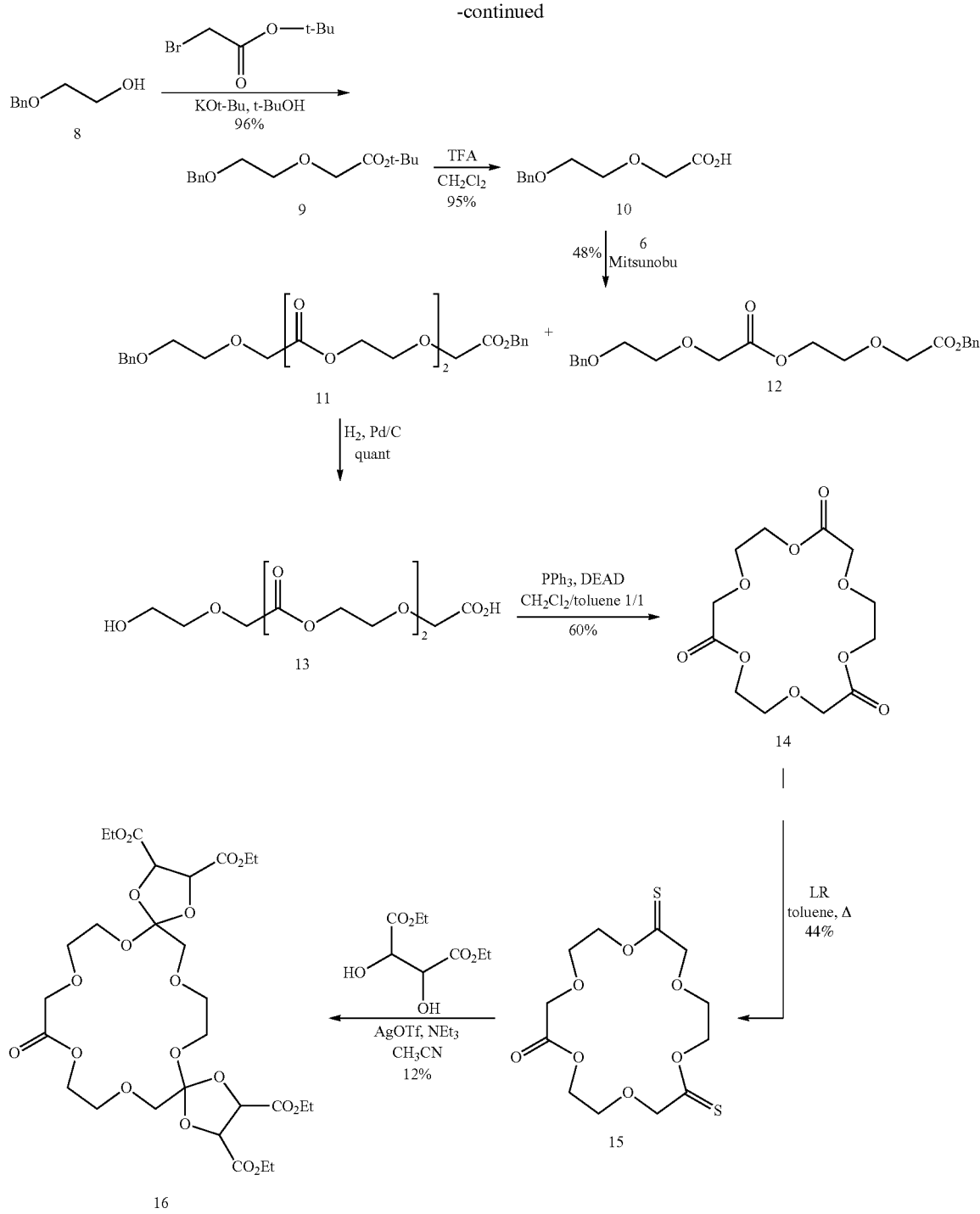

Second key precursor 10 was prepared by first coupling 2-(benzyloxy)ethanol 8 with bromoacetic acid t-butyl ester using t-BuOK as a base. Subsequent TFA treatment cleanly afforded acid 10 after aqueous work-up (acid base extraction). This synthetic sequence produced the desired acid with 91% yield for the 2 steps. In a last step, acid 10 and alcohol 6 were reacted in a Mitsunobu esterification procedure. Conversion gave a mixture of desired fully protected trimer 11 and dimer 12. Dimer formation is partly due to the presence of alcohol 7 in small amounts in the reactants, but probably also to intramolecular transesterification of the dimer alcohol prior coupling in these conditions. Thus, purification by flash chromatography afforded compounds 11 and 12 in a 75/25 ratio, and desired key compound 11 was isolated with 48% yield. Final protecting groups removal by hydrogenation afforded quantitatively seco-acid 13, which was cyclized by a Mitsunobu procedure to give compound 14 with 60% yield. This synthetic sequence allowed the obtention of cyclic HEAA derivative 14 with a 8% overall yield for 10 steps. Subsequent selective dithionation of this latter using Lawesson reagent in refluxing toluene gave dithiolactone 15 which was reacted with L-diethyl tartrate in a desulfurization/condensation process thus affording target bis-orthoester 16.

EXAMPLE 2

Further Synthetic Procedures

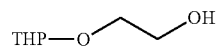

2-(tetrahydro-2H-pyran-2-yloxy)ethanol 1

A solution of ethylene glycol (22.3 ml, 0.40 mol), DHP (0.1 mol, 9 ml) and 4 drops of concentrated HCl was stirred overnight at room temperature. Mixture was then dissolved in 20% NaHCO$_2$ solution (100 ml), extracted with ether (2×50 ml) until the di-THP compound was removed (TLC). Aqueous layer was extracted with dichloromethane. Combined organic layers were dried over MgSO$_4$, filtered and concentrated to give pure compound 3 used for next step without further purification.

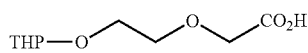

[2-(tetrahydro-2H-pyran-2-yloxy)ethoxy]acetic acid 2

To a stirred suspension of NaH (60% dispersion in mineral oil, 4.80 g, 120 mmol) in THF, at 0° C., was added a THF solution (15 ml) of bromoacetic acid (6.11 g, 44 mmol). Mixture was stirred at room temperature 0.5 hr, then a DMF solution (15 ml) of alcohol 1 (5.84 g, 40 mmol) was added dropwise. Mixture was stirred at room temperature for 17 hrs then quenched with H$_2$O and extracted twice with ether. Aqueous layer was acidified to pH 2-3 and extracted with EtOAc. Combined organic layers were dried over MgSO$_4$, filtered and concentrated to give pure compound 2 as a pale yellow oil (6.93 g, 85%) used for next step without further purification.

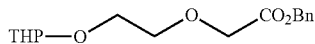

Benzyl[2-(tetrahydro-2H-pyran-2-yloxy)ethoxy]acetate 3

To a stirred solution of acid 4 (3 g, 14.71 mmol) in dichloromethane (26 ml) were added at room temperature benzyl alcohol (760 μl, 7.35 mmol), DIC (2.18 ml, 14.71 mmol) and DMAP (90 mg, 0.74 mmol). Mixture was stirred at room temperature for 3 hrs then concentrated. Purification by flash chromatography EtOAc/pentane 1/1 afforded ester 3 (2 g, 93%) as an oil.

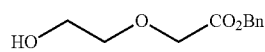

Benzyl (2-hydroxyethoxy)acetate 4

To a stirred solution of THP-protected hydroxy ester 3 (2 g, 6.8 mmol) in methanol (80 ml) was added p-TsOH (80 mg, 1 mg/ml). The reaction mixture was stirred at room temperature for 45 nm, concentrated and diluted with EtOAc. Organic layer was washed twice with NaHCO$_3$ and water, dried over MgSO$_4$, filtered and concentrated. The obtained residue was either used without further purification for next step or, if needed, purified by flash chromatography on silica gel (EtOAc/pentane 1/1) to give hydroxy ester 4 as an oil.

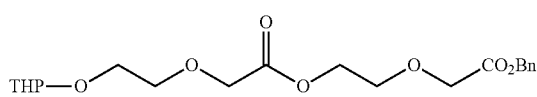

2-(2-(benzyloxy)-2-oxoethoxy)ethyl 2-(2-(tetrahydro-2H-pyran-2-yloxy)ethoxy)acetate 5

A solution of the alcohol 4 (685 mg, 3.26 mmol), the acid 2 (932 mg, 4.57 mmol), DIC (680 μl, 4.57 mmol) and DMAP (39 mg, 0.32 mmol) was stirred overnight at room temperature. The mixture was then filtered and concentrated. Flash chromatography on silica gel (EtOAc/pentane 1/1) afforded compound 5 as an oil (1.06 g, 82%).

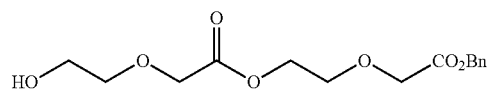

2-[2-(benzyloxy)-2-oxoethoxy]ethyl 2-(2-hydroxyethoxy)acetate 6

To a stirred solution of THP-protected hydroxy ester 5 (1 g, 2.53 mmol) in methanol (35 ml) was added p-TsOH (30 mg, 1 mg/ml). The reaction mixture was stirred at room temperature for 1 hr, concentrated and diluted with EtOAc. Organic layer was washed twice with NaHCO$_3$ and water, dried over MgSO$_4$, filtered and concentrated. The obtained oily residue (712 mg, 90%) was used for next step without further purification.

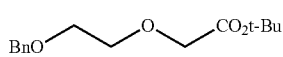

Pert-butyl[2-(benzyloxy)ethoxy]acetate 9

To a stirred solution of 2-(benzyloxy)ethanol 8 (1.7 g, 11.17 mmol) in t-BuOH (25 ml) was added at room temperature t-BuOK (1.38 g, 12.29 mmol). Mixture was stirred at room temperature for 2.5 hrs. t-butyl bromoacetate (2.7 ml, 20.11 mmol) was then added while mixture was cooled with a water bath. Mixture was stirred overnight at room temperature and concentrated. Water was added and aqueous layer was extracted with dichloromethane. Combined organic layers were dried over MgSO$_4$, filtered and concentrated. Flash chromatography on silica gel (EtOAc/pentane 1/4) afforded ester 9 as an oil (1.749 g, 59%).

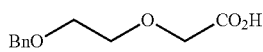

[2-(benzyloxy)ethoxy]acetic acid 10

To a stirred solution of ester 9 (2.66 g, 10 mmol) in dichloromethane (91 ml) was added TFA (9 ml) reaction mixture was stirred at room temperature for 2 hrs and mixture was concentrated. Obtained residue was diluted in water and basified with a NaOH 1N solution. This aqueous layer was extracted with ether then acidified and extracted twice with EtOAc. Combined organic layers were dried over MgSO$_4$, filtered and concentrated to give acid 10 (2 g, 95%) as an oil, used for next step without further purification.

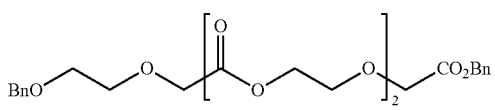

3,9-dioxo-1-phenyl-2,5,8,1'-tetraoxamidecan-13-yl 2-(2-(benzyloxy)ethoxy)acetate 11

To a stirred solution of triphenylphosphine (1.175 g, 4.48 mmol) in toluene (18 ml) at 0° C. was added DEAD (820 µl, 4.48 mmol). Mixture was stirred at 0° C. 10 min then a toluene solution (500 µl) of acid 10 (235 mg, 1.12 mmol) was added dropwise, followed by a toluene (500 µl) solution of alcohol 6 (350 mg, 1.12 mmol). Mixture was stirred 30 min at 0° C. and concentrated. Careful flash chromatography on silica gel (EtOAc/pentane 1/) afforded trimer 11 as an oil (273 mg, 48%).

$^1$H NMR (CDCl$_3$, 400 MHz): δ 7.36-7.31 (m, 5H), 5.17 (s, 2H), 4.55 (s, 2H), 4.35-4.29 (m, 4H), 4.21 (s, 2H), 4.16-4.12 (m, 4H), 3.78-3.73 (m, 6H), 3.68-3.63 (m, 2H).

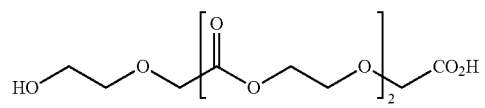

17-hydroxy-7,13-dioxo-3,6,9,12,15-pentaoxaheptadecan-1-oic acid 12

To a stirred solution of trimer 11 (168 mg) in methanol (2 ml) was added 10% Pd/C (17 mg, 10% weight). The resulting mixture was stirred for 2 hrs at room temperature. The catalyst was removed by filtration through a pad of celite and the remaining solution was concentrated, affording hydroxyacid 12 as a colorless oil (110 mg, quant.), used for next step without further purification.

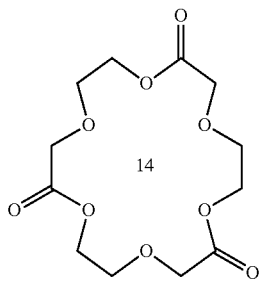 [SMILES: O=C1COCCOC(=O)COCCOC(=O)COCCO1]

1,4,7,10,13,16-hexaoxacyclooctadecane-2,8,14-trione 14

To a stirred solution of triphenylphosphine (4.68 g, 17.85 mmol) in a dichloromethane/toluene 1/1 mixture (1.5 l) was added at room temperature DEAD (8.2 ml, 44.63 mmol). Reaction mixture stirred at room temperature for 10 min then a toluene solution of hydroxyacid 12 (1.18 g, 3.57 mmol) was added. Mixture was stirred at room temperature and concentrated. Careful flash chromatography on silica gel (EtOAc/pentane 1/1 then 2/1 then EtOAc 100%) afforded cyclic 14 as a white solid (670 mg, 60%).

$^1$H NMR (CDCl$_3$, 400 MHz): δ 4.38-4.36 (m, 6H), 4.22 (s, 6H), 3.82-3.80 (m, 6H).

General Procedure for Thionation Reactions.

A solution of lactone (1 mmol) and Lawesson reagent (1.5, 7 or 8 mmol) was heated at reflux (oil bath temperature 125° C.) for 24 hrs, then allowed to cool to room temperature and filtered. Solids were washed with dichloromethane/pentane mixtures and the filtrate was concentrated. Careful purification by flash chromatography afforded thiolactone derivatives.

General Procedure for Orthoester Formation.

To a vigorously stirred solution of thiolactone (1 mmol) in acetonitrile were added at room temperature diethyl tartrate (3 or 6 mmol), followed by AgOTf (2.5 or 5 mmol, in one portion) immediately followed by dropwise addition of triethylamine (4 or 6 mmol). Mixture was stirred at room temperature for 30-45 nm then concentarted. Purification by flash chromatography afforded orthoester derivatives.

FURTHER REFERENCES

Irie and Uekama (1999), Advanced Drug Delivery Reviews 36: 101-123.
Lifson, S., Felder, C. E. and Shanzer, A. (1983), J. Am. Chem. Soc, 105, 3866-3875.
Lifson, S., Felder, C. E. and Shanzer, A. (1984), J. Am. Chem. Soc, 23, 2577-2590.
McGeary and Bruget (2000). Tetrahedron 56: 8703-8713.
Challa et al. (2005). AAPS PharmSciTech 6: E329-E357.

The invention claimed is:
1. The crown ether of any one of the preceding claims, wherein said crown ether has one of the following formulae:
Formula (III)
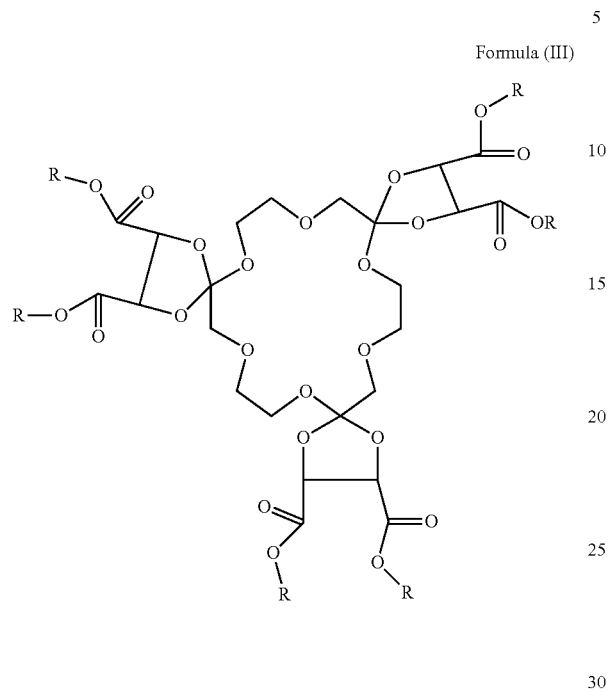
Formula (IV)
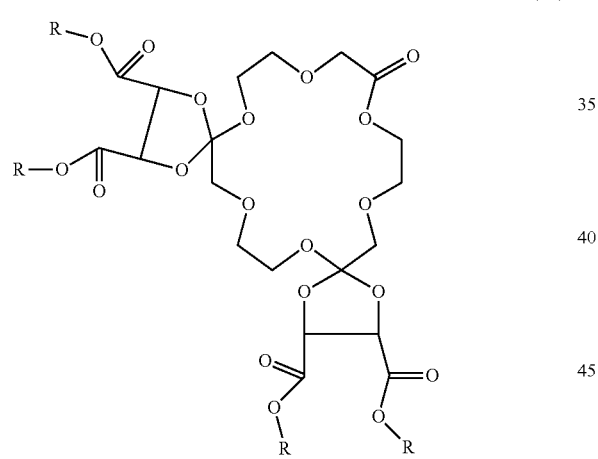
Formula (V)
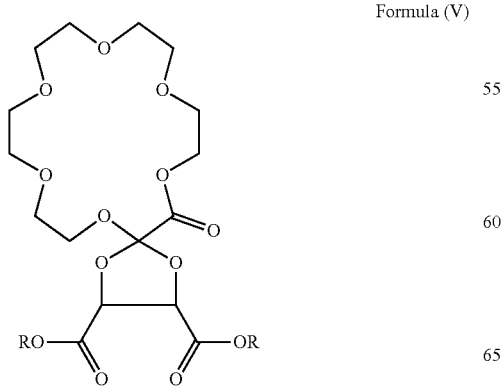
Formula (VI)
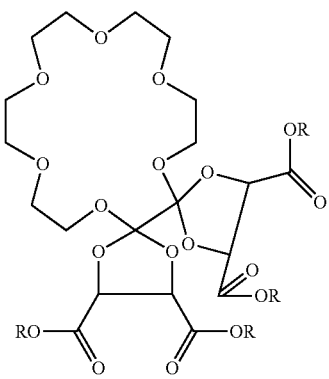
Formula (VII)
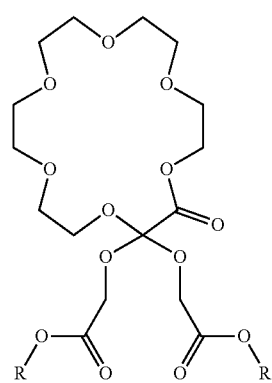
Formula (VIII)
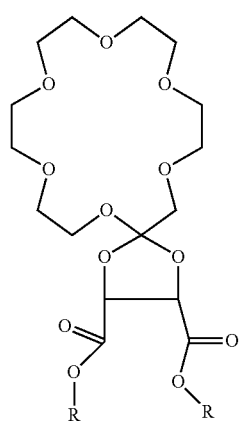

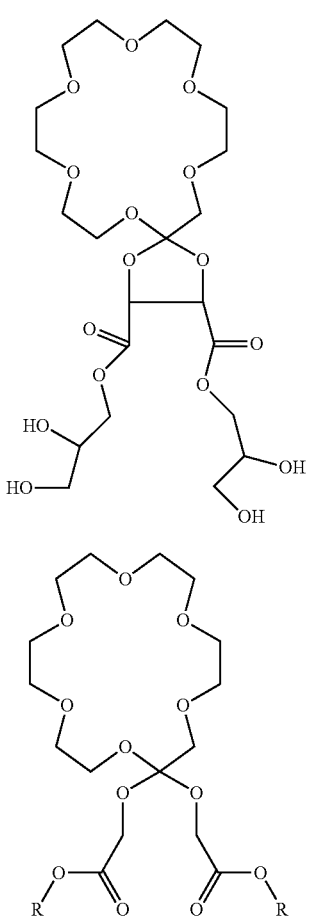

Formula (IX)

Formula (X)

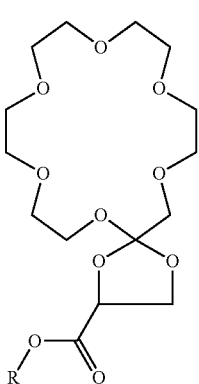

Formula (XI)

wherein R, independently for each occurrence, is selected from hydrogen; linear or branched and substituted or unsubstituted $C_1$ to $C_{10}$ alkyl; substituted or unsubstituted aryl with up to 10 ring atoms; and $H(OCH_2CH_2)_k-$, wherein k is an integer number from 1 to 10; wherein substituents, if present, are selected from OH and halogen.

2. A pharmaceutical or diagnostic composition comprising one or more crown ethers as defined in claim 1 and a pharmaceutically or diagnostically active agent, said pharmaceutically or diagnostically active agent comprising one or more primary and/or secondary protonated amino groups and/or protonated guanidinium groups and/or said pharmaceutically or diagnostically active agent is a salt with a metal ion or with an ammonium ion.

3. The pharmaceutical or diagnostic composition of claim 1 which is confectioned for transdermal and/or transmucosal delivery.

* * * * *